United States Patent
Nau, Jr. et al.

(10) Patent No.: US 11,596,476 B2
(45) Date of Patent: Mar. 7, 2023

(54) REFLECTORS FOR OPTICAL-BASED VESSEL SEALING

(71) Applicants: Covidien LP, Mansfield, MA (US); University of North Carolina at Charlotte, Charlotte, NC (US)

(72) Inventors: William H. Nau, Jr., Longmont, CO (US); Eric R. Larson, Boulder, CO (US); Duane E. Kerr, Loveland, CO (US); Nathaniel M. Fried, Concord, NC (US); Thomas C. Hutchens, Yadkinville, NC (US); Thomas W. Meiser, Lakewood, CO (US); Luke A. Hardy, Brown Summit, NC (US)

(73) Assignees: Covidien LP, Mansfield, MA (US); THE UNIVERSITY OF NORTH CARLOINA AT CHARLOTTE, Charlotte, NC (US)

( * ) Notice: Subject to any disclaimer, the term of this patent is extended or adjusted under 35 U.S.C. 154(b) by 244 days.

(21) Appl. No.: 17/080,012

(22) Filed: Oct. 26, 2020

(65) Prior Publication Data
US 2021/0038308 A1 Feb. 11, 2021

Related U.S. Application Data

(63) Continuation of application No. 15/880,312, filed on Jan. 25, 2018, now Pat. No. 10,813,695.
(Continued)

(51) Int. Cl.
*A61B 18/22* (2006.01)
*A61B 17/28* (2006.01)
(Continued)

(52) U.S. Cl.
CPC ............ *A61B 18/22* (2013.01); *A61B 17/282* (2013.01); *A61B 2018/0063* (2013.01);
(Continued)

(58) Field of Classification Search
CPC .................. A61B 18/22; A61B 17/282; A61B 2018/20554; A61B 2018/0063; A61B 2018/2035; A61B 2018/2272
(Continued)

(56) References Cited

U.S. PATENT DOCUMENTS

D249,549 S 9/1978 Pike
4,143,660 A 3/1979 Malyshev et al.
(Continued)

FOREIGN PATENT DOCUMENTS

CN 201299462 Y 9/2009
DE 2415263 A1 10/1975
(Continued)

OTHER PUBLICATIONS

Crawford et al. "Use of the LigaSure Vessel Sealing System in Urologic Cancer Surgery"; Grand Rounds in Urology 1999 vol. 1 Issue 4 pp. 10-17.
(Continued)

*Primary Examiner* — Aaron F Roane
(74) *Attorney, Agent, or Firm* — Carter, DeLuca & Farrell LLP

(57) ABSTRACT

An end effector assembly for an optical surgical instrument includes a jaw member and a plurality of optical elements positioned within a cavity of the jaw member. The jaw member has a tissue contacting surface. The jaw member has a proximal portion that is configured to secure a fiber optic cable thereto such that a distal end of the fiber optical cable extends into the cavity. The plurality of optical elements are arranged in a staircase-like manner that rises
(Continued)

towards the tissue contacting surface as the plurality of optical elements extends distally within the cavity. The plurality of optical elements is configured to direct a beam of light exiting the fiber optic cable towards the tissue contacting surface.

15 Claims, 18 Drawing Sheets

Related U.S. Application Data

(60) Provisional application No. 62/451,344, filed on Jan. 27, 2017.

(51) Int. Cl.
*A61B 18/00* (2006.01)
*A61B 18/20* (2006.01)

(52) U.S. Cl.
CPC ............... *A61B 2018/2035* (2013.01); *A61B 2018/20554* (2017.05); *A61B 2018/2272* (2013.01)

(58) Field of Classification Search
USPC .......................................................... 606/16
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| 4,757,425 A | 7/1988 | Waltz |
| D298,353 S | 11/1988 | Manno |
| D299,413 S | 1/1989 | DeCarolis |
| 5,037,433 A | 8/1991 | Wilk et al. |
| 5,055,983 A | 10/1991 | Hunold et al. |
| 5,147,356 A | 9/1992 | Bhatta |
| 5,169,396 A | 12/1992 | Dowlatshahi et al. |
| 5,209,748 A | 5/1993 | Daikuzono |
| 5,217,460 A | 6/1993 | Knoepfler |
| 5,258,006 A | 11/1993 | Rydell et al. |
| D343,453 S | 1/1994 | Noda |
| 5,318,589 A | 6/1994 | Lichtman |
| D348,930 S | 7/1994 | Olson |
| D349,341 S | 8/1994 | Lichtman et al. |
| 5,336,220 A | 8/1994 | Ryan et al. |
| 5,336,221 A | 8/1994 | Anderson |
| 5,342,358 A | 8/1994 | Daikuzono |
| 5,376,094 A | 12/1994 | Kline |
| D354,564 S | 1/1995 | Medema |
| 5,383,880 A | 1/1995 | Hooven |
| D358,887 S | 5/1995 | Feinberg |
| 5,415,657 A | 5/1995 | Taymor-Luria |
| 5,470,331 A | 11/1995 | Daikuzono |
| 5,569,241 A | 10/1996 | Edwards |
| D384,413 S | 9/1997 | Zlock et al. |
| 5,762,609 A | 6/1998 | Benaron et al. |
| H1745 H | 8/1998 | Paraschac |
| 5,800,449 A | 9/1998 | Wales |
| 5,807,393 A | 9/1998 | Williamson, IV et al. |
| 5,827,281 A | 10/1998 | Levin |
| 5,827,323 A | 10/1998 | Klieman et al. |
| D402,028 S | 12/1998 | Grimm et al. |
| 5,849,022 A | 12/1998 | Sakashita et al. |
| 5,868,760 A | 2/1999 | McGuckin, Jr. |
| D408,018 S | 4/1999 | McNaughton |
| 5,921,916 A | 7/1999 | Aeikens et al. |
| 5,957,937 A | 9/1999 | Yoon |
| D416,089 S | 11/1999 | Barton et al. |
| 5,993,466 A | 11/1999 | Yoon |
| 5,993,467 A | 11/1999 | Yoon |
| 6,004,332 A | 12/1999 | Yoon et al. |
| 6,024,741 A | 2/2000 | Williamson, IV et al. |
| 6,039,729 A | 3/2000 | Durville et al. |
| 6,053,909 A | 4/2000 | Shadduck |
| 6,053,933 A | 4/2000 | Balazs et al. |
| D424,694 S | 5/2000 | Tetzlaff et al. |
| D425,201 S | 5/2000 | Tetzlaff et al. |
| 6,086,601 A | 7/2000 | Yoon |
| H1904 H | 10/2000 | Yates et al. |
| 6,126,665 A | 10/2000 | Yoon |
| 6,143,005 A | 11/2000 | Yoon et al. |
| 6,224,614 B1 | 5/2001 | Yoon |
| 6,283,961 B1 | 9/2001 | Underwood et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,443,970 B1 | 9/2002 | Schulze et al. |
| D465,281 S | 11/2002 | Lang |
| D466,209 S | 11/2002 | Bon |
| 6,508,816 B2 | 1/2003 | Shadduck |
| 6,626,901 B1 | 9/2003 | Treat et al. |
| 6,663,639 B1 | 12/2003 | Laufer et al. |
| 6,689,131 B2 | 2/2004 | McClurken |
| 6,726,694 B2 | 4/2004 | Blatter et al. |
| 6,743,239 B1 | 6/2004 | Kuehn et al. |
| D493,888 S | 8/2004 | Reschke |
| 6,773,409 B2 | 8/2004 | Truckai et al. |
| 6,773,441 B1 | 8/2004 | Laufer et al. |
| 6,786,905 B2 | 9/2004 | Swanson et al. |
| D496,997 S | 10/2004 | Dycus et al. |
| D499,181 S | 11/2004 | Dycus et al. |
| D502,994 S | 3/2005 | Blake, III |
| 6,860,880 B2 | 3/2005 | Treat et al. |
| 6,908,463 B2 | 6/2005 | Treat et al. |
| 6,932,816 B2 | 8/2005 | Phan |
| D509,297 S | 9/2005 | Wells |
| 7,052,489 B2 | 5/2006 | Griego et al. |
| D525,361 S | 7/2006 | Hushka |
| D531,311 S | 10/2006 | Guerra et al. |
| 7,115,139 B2 | 10/2006 | McClurken et al. |
| D533,274 S | 12/2006 | Visconti et al. |
| D533,942 S | 12/2006 | Kerr et al. |
| D535,027 S | 1/2007 | James et al. |
| 7,160,299 B2 | 1/2007 | Baily |
| 7,169,146 B2 | 1/2007 | Truckai et al. |
| 7,179,255 B2 | 2/2007 | Lettice et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,318,823 B2 | 1/2008 | Sharps et al. |
| D564,662 S | 3/2008 | Moses et al. |
| D567,943 S | 4/2008 | Moses et al. |
| 7,367,976 B2 | 5/2008 | Lawes et al. |
| D575,395 S | 8/2008 | Hushka |
| D575,401 S | 8/2008 | Hixson et al. |
| 7,414,724 B2 | 8/2008 | Eckert et al. |
| D582,038 S | 12/2008 | Swoyer et al. |
| 7,588,565 B2 | 9/2009 | Marchitto et al. |
| 7,655,007 B2 | 2/2010 | Baily |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,753,908 B2 | 7/2010 | Swanson |
| D621,503 S | 8/2010 | Otten et al. |
| 7,775,103 B2 | 8/2010 | Veerasamy |
| D627,462 S | 11/2010 | Kingsley |
| D628,289 S | 11/2010 | Romero |
| D628,290 S | 11/2010 | Romero |
| D630,324 S | 1/2011 | Reschke |
| 7,967,839 B2 | 6/2011 | Flock et al. |
| 8,012,166 B2 | 9/2011 | Rizvi |
| D649,249 S | 11/2011 | Guerra |

(56) References Cited

U.S. PATENT DOCUMENTS

| | | |
|---|---|---|
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 8,469,716 B2 | 6/2013 | Fedotov et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,898,888 B2 | 12/2014 | Brandt et al. |
| 8,900,232 B2 | 12/2014 | Ourada |
| 8,920,421 B2 | 12/2014 | Rupp |
| 8,932,293 B2 | 1/2015 | Chernov et al. |
| 8,936,614 B2 | 1/2015 | Allen, IV |
| 8,939,572 B2 | 1/2015 | Perez Gellida et al. |
| 8,945,175 B2 | 2/2015 | Twomey |
| 8,961,513 B2 | 2/2015 | Allen, IV et al. |
| 8,961,515 B2 | 2/2015 | Twomey et al. |
| 8,968,283 B2 | 3/2015 | Kharin |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,316 B2 | 3/2015 | Roy et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,484 B2 | 5/2015 | Craig |
| 9,028,492 B2 | 5/2015 | Kerr et al. |
| 9,039,704 B2 | 5/2015 | Joseph |
| 9,039,732 B2 | 5/2015 | Sims et al. |
| 9,060,780 B2 | 6/2015 | Twomey et al. |
| 9,084,608 B2 | 7/2015 | Larson et al. |
| 9,113,882 B2 | 8/2015 | Twomey et al. |
| 9,113,899 B2 | 8/2015 | Garrison et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,113,940 B2 | 8/2015 | Twomey |
| 9,161,807 B2 | 10/2015 | Garrison |
| 9,211,657 B2 | 12/2015 | Ackley et al. |
| 9,216,700 B2 | 12/2015 | Gordon |
| 9,259,268 B2 | 2/2016 | Behnke, II et al. |
| 9,265,565 B2 | 2/2016 | Kerr |
| 9,265,568 B2 | 2/2016 | Chernov et al. |
| 9,314,295 B2 | 4/2016 | Garrison |
| 9,333,002 B2 | 5/2016 | Garrison |
| 9,375,282 B2 | 6/2016 | Nau, Jr. et al. |
| 9,381,059 B2 | 7/2016 | Garrison |
| 9,610,121 B2 | 4/2017 | Nau, Jr. et al. |
| 9,925,008 B2 | 3/2018 | Nau, Jr. et al. |
| 2003/0069571 A1 | 4/2003 | Treat et al. |
| 2003/0120306 A1 | 6/2003 | Burbank et al. |
| 2003/0158548 A1 | 8/2003 | Phan et al. |
| 2003/0158549 A1 | 8/2003 | Swanson |
| 2003/0171741 A1 | 9/2003 | Ziebol et al. |
| 2003/0195559 A1 | 10/2003 | Colgan |
| 2003/0216732 A1 | 11/2003 | Truckai et al. |
| 2003/0236518 A1 | 12/2003 | Marchitto et al. |
| 2004/0073256 A1 | 4/2004 | Marchitto et al. |
| 2004/0210282 A1 | 10/2004 | Flock et al. |
| 2004/0260281 A1 | 12/2004 | Baxter et al. |
| 2005/0033278 A1 | 2/2005 | McClurken et al. |
| 2005/0059934 A1 | 3/2005 | Wenchell et al. |
| 2005/0131390 A1 | 6/2005 | Heinrich et al. |
| 2006/0195165 A1 | 8/2006 | Gertner et al. |
| 2006/0224154 A1 | 10/2006 | Shadduck et al. |
| 2007/0156140 A1 | 7/2007 | Baily |
| 2007/0167678 A1 | 7/2007 | Moskowitz et al. |
| 2007/0225695 A1 | 9/2007 | Mayer et al. |
| 2008/0046122 A1 | 2/2008 | Manzo et al. |
| 2008/0247594 A1 | 10/2008 | Leclear et al. |
| 2008/0281311 A1 | 11/2008 | Dunning et al. |
| 2008/0283577 A1 | 11/2008 | Boyden et al. |
| 2008/0319442 A1 | 12/2008 | Unger et al. |
| 2009/0138029 A1 | 5/2009 | Saliman et al. |
| 2009/0145194 A1 | 6/2009 | Clayton et al. |
| 2009/0318912 A1 | 12/2009 | Mayer et al. |
| 2010/0049187 A1 | 2/2010 | Carlton et al. |
| 2010/0063500 A1 | 3/2010 | Muszala |
| 2010/0094271 A1 | 4/2010 | Ward et al. |
| 2010/0100122 A1 | 4/2010 | Hinton |
| 2010/0130971 A1 | 5/2010 | Baily |
| 2010/0228249 A1 | 9/2010 | Mohr et al. |
| 2011/0087202 A1 | 4/2011 | Lewinsky et al. |
| 2011/0224485 A1 | 9/2011 | Boulnois et al. |
| 2011/0251605 A1 | 10/2011 | Hoarau et al. |
| 2012/0209263 A1 | 8/2012 | Sharp et al. |
| 2012/0296205 A1 | 11/2012 | Chernov et al. |
| 2012/0296238 A1 | 11/2012 | Chernov et al. |
| 2012/0296323 A1 | 11/2012 | Chernov et al. |
| 2012/0323238 A1 | 12/2012 | Tyrrell et al. |
| 2013/0018364 A1 | 1/2013 | Chernov et al. |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079774 A1 | 3/2013 | Whitney et al. |
| 2013/0085496 A1 | 4/2013 | Unger et al. |
| 2013/0103017 A1 | 4/2013 | Weckwerth |
| 2013/0103031 A1 | 4/2013 | Garrison |
| 2013/0197503 A1 | 8/2013 | Orszulak |
| 2013/0253489 A1* | 9/2013 | Nau, Jr. .............. A61B 17/29 606/17 |
| 2014/0066911 A1 | 3/2014 | Nau, Jr. |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | Mccullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | Mckenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |

(56) References Cited

U.S. PATENT DOCUMENTS

| | | | |
|---|---|---|---|
| 2015/0088126 A1 | 3/2015 | Duffin et al. | |
| 2015/0088128 A1 | 3/2015 | Couture | |
| 2015/0094714 A1 | 4/2015 | Lee et al. | |
| 2016/0346034 A1 | 12/2016 | Arya et al. | |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 3/1988 |
| DE | 3712328 A1 | 10/1988 |
| DE | 04303882 C2 | 2/1995 |
| DE | 04403252 A1 | 8/1995 |
| DE | 4434938 C1 | 2/1996 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 0480293 A1 | 4/1992 |
| EP | 0589555 A1 | 3/1994 |
| EP | 0776739 A2 | 6/1997 |
| EP | 1177771 A1 | 2/2002 |
| EP | 1278007 A1 | 1/2003 |
| EP | 1281878 A1 | 2/2003 |
| EP | 1159926 A2 | 3/2003 |
| EP | 1842500 A2 | 10/2007 |
| EP | 2113218 A2 | 11/2009 |
| EP | 02241280 A2 | 10/2010 |
| JP | 53145385 | 12/1978 |
| JP | 61501068 | 9/1984 |
| JP | 1024051 A | 1/1989 |
| JP | 1147150 A | 6/1989 |
| JP | 6502328 | 3/1992 |
| JP | 55106 | 1/1993 |
| JP | H0540112 A | 2/1993 |
| JP | 0006030945 | 2/1994 |
| JP | 6121797 A | 5/1994 |
| JP | 6285078 A | 10/1994 |
| JP | 6511401 | 12/1994 |
| JP | H06343644 A | 12/1994 |
| JP | 07265328 | 10/1995 |
| JP | H07265328 A | 10/1995 |
| JP | 08056955 | 3/1996 |
| JP | 08098799 A | 4/1996 |
| JP | H08503626 A | 4/1996 |
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 09000538 A | 1/1997 |
| JP | H0910223 A | 1/1997 |
| JP | 9122138 A | 5/1997 |
| JP | 0010000195 A | 1/1998 |
| JP | 10155798 A | 6/1998 |
| JP | 1147149 | 2/1999 |
| JP | 11070124 A | 3/1999 |
| JP | 11169381 A | 6/1999 |
| JP | 11192238 A | 7/1999 |
| JP | 11244298 | 9/1999 |
| JP | H11244298 A | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 | 1/2001 |
| JP | 2001029355 | 2/2001 |
| JP | 2001029356 | 2/2001 |
| JP | 2001003400 | 4/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | 6030945 B2 | 11/2016 |
| JP | H0630945 B2 | 11/2016 |
| SU | 401367 A1 | 11/1974 |
| WO | 8503781 A1 | 8/1985 |
| WO | 9408526 A1 | 4/1994 |
| WO | 9814124 A1 | 4/1998 |
| WO | 0036986 A1 | 6/2000 |
| WO | 0059392 A1 | 10/2000 |
| WO | 0101847 A1 | 1/2001 |
| WO | 0115614 A1 | 3/2001 |
| WO | 0154604 A1 | 8/2001 |
| WO | 0245589 | 6/2002 |
| WO | 03090630 A2 | 11/2003 |
| WO | 2006021269 A1 | 3/2006 |
| WO | 2005110264 A2 | 4/2006 |
| WO | 2007032900 A2 | 3/2007 |
| WO | 2008040483 A1 | 4/2008 |
| WO | 20080112147 A1 | 9/2008 |
| WO | 20090005850 A1 | 1/2009 |
| WO | 2010060097 A2 | 5/2010 |
| WO | 2010104753 A1 | 9/2010 |
| WO | 2011018154 A1 | 2/2011 |
| WO | 2012158 A1 | 11/2012 |
| WO | 2012158788 A1 | 11/2012 |

OTHER PUBLICATIONS

Koyle et al., "Laparoscopic Palomo Varicocele Ligation in Children and Adolescents" Pediatric Endosurgery & Innovative Techniques, vol. 6, No. 1, 2002.

Sengupta et al., "Use of a Computer-Controlled Bipolar Diathermy System in Radical Prostatectomies and Other Open Urological Surgery" ANZ Journal of Surgery (2001) 71.9 pp. 538-540.

Peterson et al. "Comparison of Healing Process Following Ligation with Sutures and Bipolar Vessel Sealing" Surgical Technology International (2001).

Heniford et al. "Initial Research and Clinical Results with an Electrothermal Bipolar Vessel Sealer" Oct. 1999.

Herman et al., "Laparoscopic Intestinal Resection With the LigaSure Vessel Sealing System: A Case Report"; Innovations That Work, Feb. 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparoscopic Surgery; Sales/Product Literature; Apr. 2002.

Sigel et al. "The Mechanism of Blood Vessel Closure by High Frequency Electrocoagulation" Surgery Gynecology & Obstetrics, Oct. 1965 pp. 823-831.

(56) References Cited

OTHER PUBLICATIONS

Sampayan et al., "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Rothenberg et al. "Use of the LigaSure Vessel Sealing System in Minimally Invasive Surgery in Children" Int'l Pediatric Endosurgery Group (IPEG) 2000.
McLellan et al. "Vessel Sealing for Hemostasis During Gynecologic Surgery" Sales/Product Literature 1999.
"Electrosurgery: A Historical Overview" Innovations in Electrosurgery; Sales/Product Literature; Dec. 31, 2000. (6 pages).
Johnson et al. "Evaluation of a Bipolar Electrothermal Vessel Sealing Device in Hemorrhoidectomy" Sales/Product Literature; Jan. 2004. (1 page).
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Heniford et al. "Initial Results with an Electrothermal Bipolar Vessel Sealer" Surgical Endoscopy (2000) 15:799-801. (4 pages).
"Reducing Needlestick Injuries in the Operating Room" Sales/Product Literature 2001. (1 page).
Levy et al., "Update on Hysterectomy—New Technologies and Techniques" OBG Management, Feb. 2003. (15 pages).
Barbara Levy, "Use of a New Vessel Ligation Device During Vaginal Hysterectomy" FIGO 2000, Washington, D.C.. (1 page).
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Johnson et al. "Evaluation of the LigaSure Vessel Sealing System in Hemorrhoidectormy" American College of Surgeons (ACS) Clinicla Congress Poster (2000).
Joseph Ortenberg "LigaSure System Used in Laparoscopic 1st and 2nd Stage Orchiopexy" Innovations That Work, Nov. 2002.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
E. David Crawford "Evaluation of a New Vessel Sealing Device in Urologic Cancer Surgery" Sales/Product Literature 2000.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
E. David Crawford "Use of a Novel Vessel Sealing Technology in Management of the Dorsal Veinous Complex" Sales/Product Literature 2000.
Crawford et al. "Use of the LigaSure Vessel Sealing System in Urologic Cancer Surger" Grand Rounds in Urology 1999 vol. 1 Issue 4 pp. 10-17.
Bergdahl et al. "Studies on Coagulation and the Development of an Automatic Computerized Bipolar Coagulator" J. Neurosurg, vol. 75, Jul. 1991, pp. 148-151.
Levy et al. "Use of a New Energy-based Vessel Ligation Device During Vaginal Hysterectomy" Int'l Federation of Gynecology and Obstetrics (FIGO) World Congress 1999.
Olsson et al. "Radical Cystectomy in Females" Current Surgical Techniques in Urology, vol. 14, Issue 3, 2001.
Sayfan et al. "Sutureless Closed Hemorrhoidectomy: A New Technique" Annals of Surgery vol. 234 No. 1 Jul. 2001; pp. 21-24.
Craig Johnson, "Use of the LigaSure Vessel Sealing System in Bloodless Hemorrhoidectomy" Innovations That Work, Mar. 2000.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Muller et al., "Extended Left Hemicolectomy Using the LigaSure Vessel Sealing System" Innovations That Work, Sep. 1999.
Carus et al., "Initial Experience With the LigaSure Vessel Sealing System in Abdominal Surgery" Innovations That Work, Jun. 2002.
Jarrett et al., "Use of the LigaSure Vessel Sealing System for Peri-Hilar Vessels in Laparoscopic Nephrectomy" Sales/Product Literature 2000.
Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.
European Search Report dated Jul. 4, 2018 in EP Appln. No. 18153733.

* cited by examiner

REFLECTORS FOR OPTICAL-BASED VESSEL SEALING

CROSS-REFERENCE TO RELATED APPLICATION

This application is a continuation of U.S. patent application Ser. No. 15/880,312, filed Jan. 25, 2018, which claims priority to, and benefit of, U.S. Provisional Patent Application Ser. No. 62/451,344, filed Jan. 27, 2017, the entire contents of which is hereby incorporated by reference.

BACKGROUND

1. Technical Field

The present disclosure relates to surgical instruments and, more specifically, to surgical instruments for sealing vessels with optical energy.

2. Discussion of Related Art

In many surgical procedures, body vessels, e.g., blood vessels, ducts, adhesions, fallopian tubes, or the like are sealed to defunctionalize or close the vessels. Traditionally, staples, clips or sutures have been used to close a body vessel. However, these traditional procedures often leave foreign body material inside a patient. In an effort to reduce foreign body material left within the patient and to more effectively close off the body vessel, energy techniques that seal by heating tissue have been employed.

Endoscopic or open forceps are particularly useful for sealing since forceps utilize mechanical action to constrict, grasp, dissect, and/or clamp tissue. Current vessel sealing procedures utilize electrosurgical energy in the form of electrical, radio frequency, ultrasonic, or microwave energy to heat vessels or tissue causing closure and sealing of vessels or tissue. When tissue is sealed with electrosurgical energy, there is a desire to minimize heating of surrounding tissue. In addition, after tissue is sealed, it may be advantageous to sever or cut the tissue with either electrosurgical energy and/or with a mechanical knife.

SUMMARY

There is a continuing need for surgical instruments that can seal and/or cut tissue while minimizing the heating of surrounding tissue.

This disclosure relates generally to surgical instruments that use optical energy to seal and/or cut tissue. Specifically, surgical instruments that have an end effector assembly including a jaw member that has a plurality of optical elements that shape a beam of light towards tissue grasped within the end effector assembly such that a distribution of energy from the beam of light is configured to seal and/or cut the tissue.

In an aspect of the present disclosure, an end effector assembly for an optical surgical instrument includes a jaw member and a plurality of optical elements positioned within a cavity of the jaw member. The jaw member has a tissue contacting surface. The jaw member has a proximal portion that is configured to secure a fiber optic cable thereto such that a distal end of the fiber optical cable extends into the cavity. The plurality of optical elements are arranged in a staircase-like manner that rises towards the tissue contacting surface as the plurality of optical elements extends distally within the cavity. The plurality of optical elements is configured to direct a beam of light exiting the fiber optic cable towards the tissue contacting surface.

In aspects, each optical element of the plurality of optical elements is substantially cylindrical in shape and arranged transverse to a longitudinal axis defined through the jaw member. Each optical element of the plurality of optical elements may have the same diameter.

In some aspects, the plurality of optical elements includes a first series of optical elements and a second series of optical elements. The first series of optical elements may be rotated relative to a base plane that is parallel to the tissue contacting surface in a first direction. The second series of the optical elements may be rotated relative to the base plane in a second direction. The first series of optical elements may be rotated at a first angle and the second series of optical elements may be rotated at a second angle. The second angle may be different from the first angle.

In certain aspects, at least one of the plurality of optical elements is curved away from the tissue contacting surface such that the at least one of the plurality of optical elements is substantially u-shaped in cross-section transverse to a longitudinal axis defined through the jaw member. The at least one of the plurality of optical elements may have a parabolic cross-section transverse to the longitudinal axis.

In particular aspects, the end effector assembly includes a cartridge that is configured to be secured within the cavity. The cartridge may include the plurality of optical elements.

In aspects, the end effector assembly includes a cover that is disposed over the cavity. The cover may be configured to modify light reflected from the plurality of optical elements. The cover may be configured to at least one of filter, refract, or diffuse light reflected from the plurality of optical elements. The cover may be configured to seal the cavity.

In some aspects, the first jaw member is curved. The end effector assembly may include an opposing jaw member that has an opposing tissue contacting surface in opposition to the tissue contacting surface of the jaw member. The opposing tissue contacting surface may be configured to absorb light.

In another aspect of the present disclosure, a surgical instrument includes a handle, an elongated body extending from the handle, a fiber optic cable, and an end effector assembly. The fiber optic cable extends from the handle and through the elongated body. The end effector assembly is secured to a distal portion of the elongated body and includes a first jaw member, a second jaw member, and a plurality of optical elements. The first jaw member includes a first tissue contacting surface and the second jaw member includes a second tissue contacting surface that opposes the first tissue contacting surface. The second jaw member defines a cavity and has a proximal portion. A distal portion of the fiber optic cable extends into the proximal portion of the second jaw member and is configured to emit light into the cavity. The plurality of optical elements is positioned within the cavity and arranged in a staircase-like manner that rises towards the second tissue contacting surface as the staircase extends distally within the cavity. The plurality of optical elements is configured to direct a beam of light exiting the fiber optic cable towards the tissue contacting surface of the second jaw member.

In aspects, the handle includes a light source that is coupled to a proximal end of the fiber optic cable. The light source may be configured to generate the beam of light. The end effector assembly may be configured to cut tissue with optical energy.

In another aspect of the present disclosure, a method of treating tissue includes grasping tissue between first and second jaw members and activating a light source such that light is emitted from the first jaw member, the light reflected by a plurality of optical elements disposed within the first jaw member such that optical energy is reflected towards a tissue contacting surface of the first jaw member.

In aspects, activating the light source includes the optical energy sealing the tissue between the first and second jaw members. The method may include activating the light source to cut the tissue subsequent to sealing the tissue.

In some aspects, activating the light source includes the optical energy cutting the tissue between the first and second jaw members.

In particular aspects, the method includes selecting a cartridge based on a type of tissue. The cartridge may include the plurality of optical elements. Selecting the cartridge may include selecting the cartridge from a plurality of cartridges. Selecting the cartridge may include selecting the cartridge to cut tissue with optical energy.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
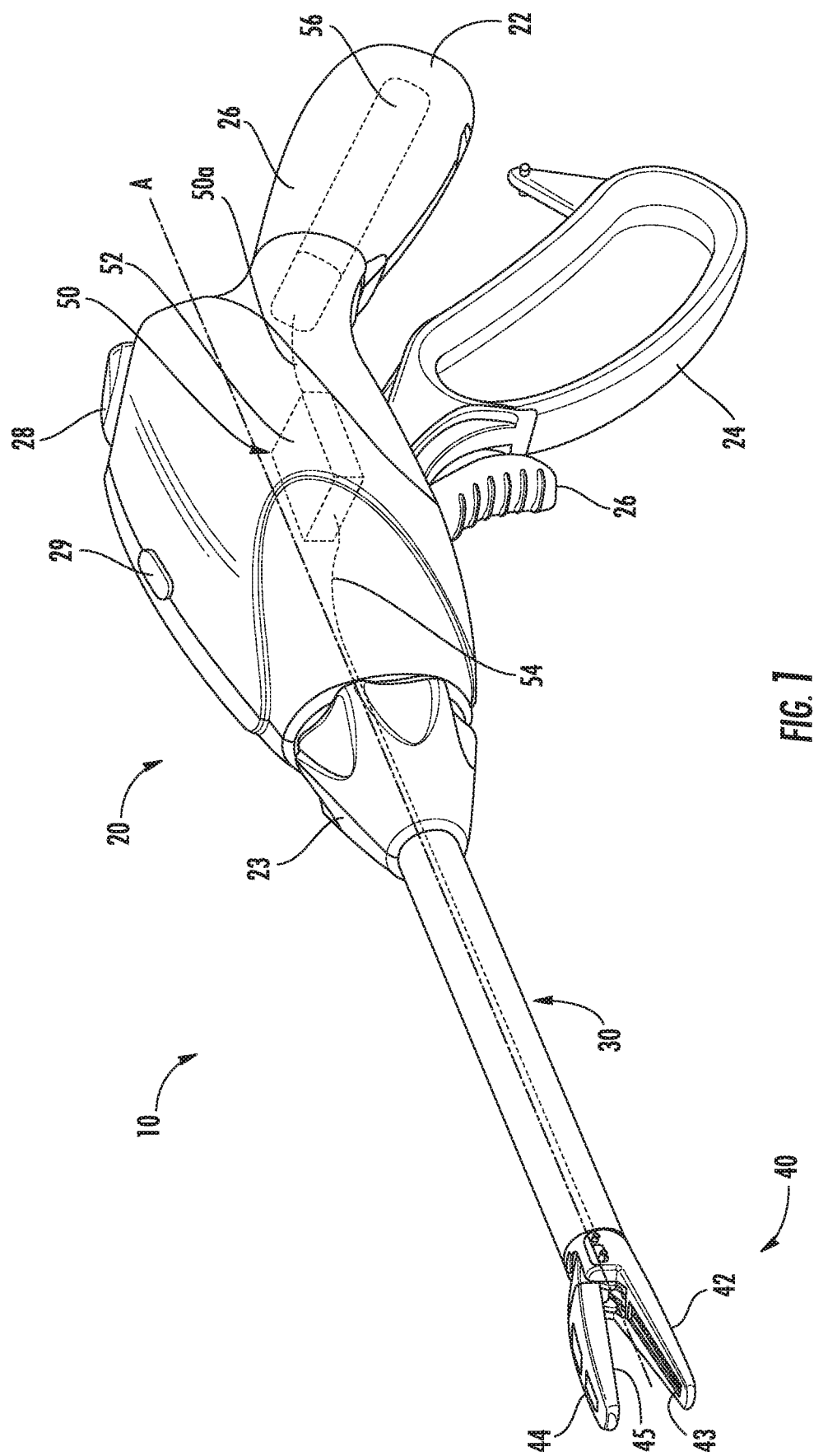
FIG. 1 is a perspective view of a surgical instrument including an optical array provided in accordance with an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician. As used herein, the term "light source" broadly refers to all types of devices or elements that generate or transmit light for medical use (e.g., tissue treatment). These devices include lasers, light emitting diodes (LEDs), lamps, and other devices that generate light having a wavelength that is within the light spectrum (e.g., from infrared light to ultraviolet light). Also, the light sources described herein may be used interchangeably. For example, in some embodiments, an LED light source may be used interchangeably with a laser light source.

This disclosure describes a concept that facilitates shaping the optical energy across and along a sealing surface of an optical-based vessel sealing instruments and may be applicable to any optical-based tissue treatment instruments. Such optical based systems and devices have been shown to seal and/or cut vessels having a diameter of up to 9 mm and are envisioned to be capable of sealing and/or cutting vessels having a diameter greater than 9 mm. In addition, the optical-based vessel sealing instruments allows for cutting tissue without a mechanical blade.

Referring now to FIG. 1, a surgical instrument 10 is provided in accordance with the present disclosure. The surgical instrument 10 includes a handle assembly 20, an elongated body 30, and an end effector assembly 40 supported by a distal portion of the elongated body 30. The handle assembly 20 includes a fixed handle 22 and one or more control interfaces configured to manipulate the end effector assembly 40. For example, the handle assembly 20 may include one or more control interfaces, e.g., a movable handle 24, a trigger 26, a switch 28, and a button 29. The handle assembly 20 may also include a rotation control 23 configured to rotate the elongated body 30, and the end effector assembly 40, relative to the handle assembly 20 about a longitudinal axis A-A defined by the elongated body 30.

Figure 2:
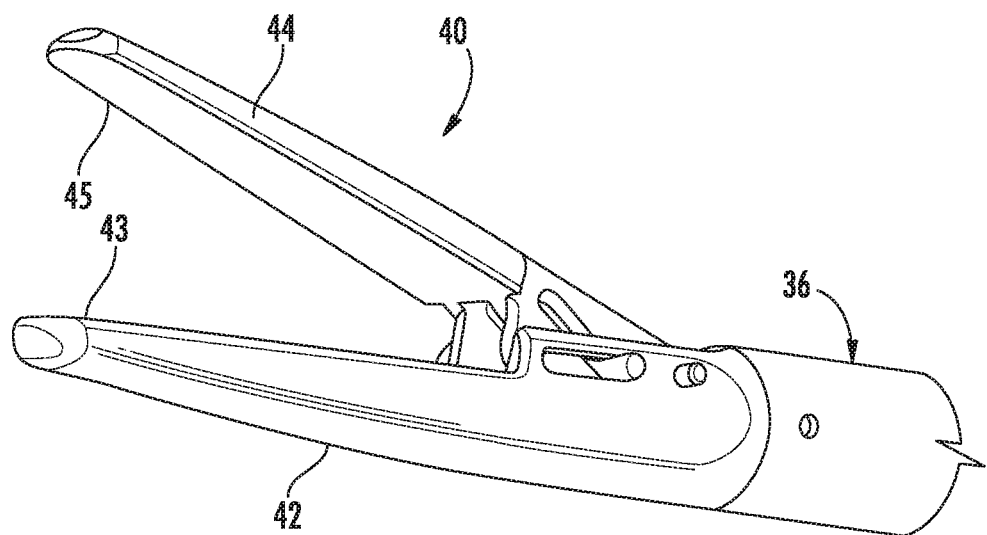
FIG. 2 is an enlarged perspective view of an end effector of the surgical instrument of FIG. 1.

With additional reference to FIG. 2, the end effector assembly 40 includes a first jaw member 42 and a second jaw member 44. The first jaw member 42 has a first tissue contacting surface 43 and the second jaw member 44 has a second tissue contacting surface 45. As shown the first and second jaw members 42, 44 are pivotable relative to one another between a spaced-apart configuration in which the first and second tissue contacting surfaces 43, 45 are spaced-apart from one another and an approximated position in which the first and second tissue contacting surfaces 43, 45 are configured to grasp tissue therebetween. In some embodiments, one of the first and second jaw members 42, 44 is fixed relative to the elongated member 30 and the other one of the first and second jaw members 42, 44 is pivotable relative to the fixed jaw member. As shown, the first and second jaw members 42, 44 are linear extending in a direction parallel to the longitudinal axis A-A.

The first and/or second jaw members 42, 44 may include stop members (not shown) configured to maintain a gap distance between the first and second jaw members 42, 44 during a surgical procedure. The gap distance and/or pressure between the first and second jaw members 42, 44 may affect sealing and/or cutting tissue between the first and second jaw members 42, 44. The stop members may be adjustable to vary the gap distance and/or pressure before, during, or after a sealing or cutting procedure.

Figure 3:
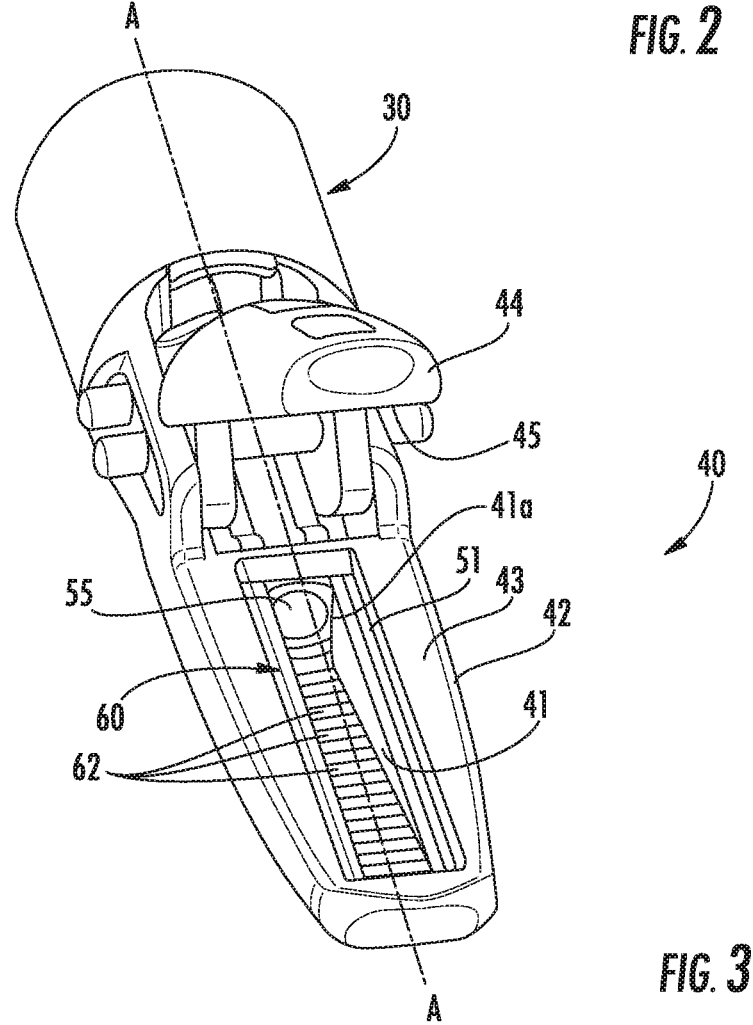
FIG. 3 is a front perspective view of the end effector of FIG. 2.

Referring briefly back to FIG. 1, the surgical instrument 10 also includes an optical system 50 configured to generate and transmit light into and/or through tissue positioned between the first and second jaw members 42, 44 to seal, coagulate, and/or cut the tissue. The optical system 50 includes a light source 52 and an optical array 60 (FIG. 3). The optical array 60 is disposed within the first jaw member 42. As shown, the optical array 60 is shown in the first jaw member 42, in some embodiments, the optical array 60 is disposed in the second jaw member 44. In addition, in embodiments, both the first and second jaw members 42, 44 each include an optical array similar to the optical array 60 detailed below.

The light source 52 is disposed within the handle assembly 20 and is optically coupled to the end effector assembly 40 by one or more transmissive elements 54 that pass through the elongated member 30. The transmissive element 54 may include fiber optic cables that pass through the elongated member 30. The optical system 50 may include an energy source 56 disposed within the handle assembly 20 or may be coupled to an external source of energy (not shown). In some embodiments, the light source 52 for the optical system 50 is external to the surgical instrument 10 and is optically coupled to the end effector assembly 40 by the transmissive element 54. In such embodiments, the transmissive element 54 may extend through the handle assembly 20 and/or the elongated member 30. Alternatively, the transmissive element 54 may be configured to not pass through the elongated member 30 and/or the handle assembly 20.

The light source 52 is configured to transmit a beam of light L (FIG. 4) having a therapeutic wavelength such that energy from the beam of light L is configured to seal, coagulate, and/or cut tissue. The light source 52 may be a near-infrared laser source having a wavelength λ in a range of about 800 nm to about 1550 nm. Other or additional wavelengths may be used to seal and/or cut tissue.

Figure 4:
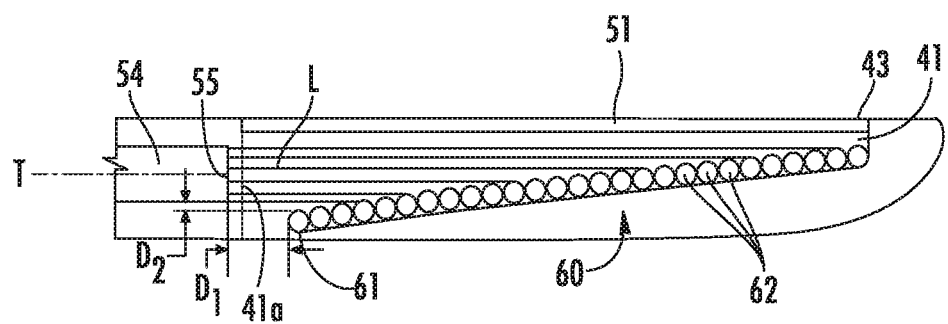
FIG. 4 is a side cutaway view of a jaw member of the end effector of FIG. 3.

With reference to FIGS. 2-4, the construction of the optical array 60 and the first jaw member 42 are detailed in accordance with the present disclosure. The first jaw member 42 defines a cavity 41 and an opening 41a that is in communication with the cavity 41. The walls defining the cavity 41 may be coated with a reflective material to reflect light contacting the walls. For example, the walls defining the cavity 41 may be coated with gold and polished to minimize absorption of light; however, other materials are also contemplated. In some embodiments, the opening 41a may include a lens (not shown) configured to aim or converge the beam towards the optical element(s) 62. In embodiments, opening 41a may include a diffusing grating that is configured to diffuse light.

The second tissue contacting surface 45 of the second jaw member 44 may also be coated or plated with a reflective material to minimize absorption of light. For example, the tissue contacting surface 45 may be coated with gold and polished to minimize absorption of light. Alternatively, the second tissue contacting surface 45 of the second jaw member 44 may be coated with a material configured to maximize absorption of light such that light that passes through tissue between the first and second jaw members 42, 44 is absorbed by the second tissue contacting surface 45.

In some embodiments, the second jaw member 44 has a construction similar to that of the first jaw member 42 detailed below such that the first and second jaw members 42, 44 are each configured to transmit light through tissue disposed between the first and second jaw members 42, 44. In such embodiments, the optical elements of the first jaw member 42 may be configured to transmit light to seal tissue and the optical elements of the second jaw member 44 may be configured to cut tissue simultaneous with or subsequent to the sealing of the tissue.

The first jaw member 42 includes a plurality of optical reflectors or elements 62 in optical communication with the light source 52 (FIG. 1) via the transmissive element 54. Specifically, a distal portion of the transmissive element 54 is secured within a proximal portion of the first jaw member 42. A distal end 55 of the transmissive element 54 is positioned such that a beam of light L transmitted from the distal end 55 of the transmissive element 54 is directed towards the plurality of optical reflectors 62. The distal portion of the transmissive element 54 is secured such that the distal end 55 is a distance $D_1$ from a bottom or first cylinder 61 of the optical elements 62 and a distance $D_2$ above the bottom or first cylinder 61 of the plurality of optical reflectors 62. The distances $D_1$ and $D_2$ affect the distribution of energy from the beam of light L. It is contemplated that $D_1$ may be in a range of about 0.25 mm to about 4 mm and that $D_2$ may be in a range of about 0.0 mm to about 3 mm The transmissive element 54 defines a transmission axis T-T which is aligned with a beam of light transmitted from the distal end 55 of the transmissive element 54. The transmission axis T-T is parallel to the longitudinal axis A-A or may define a transmission angle α with the longitudinal axis A-A. The transmission angle α may have a first component defined in a plane extending perpendicular to the first tissue contacting surface 43 and parallel to the longitudinal axis A-A in a range of 0 degrees to about ±10 degrees and may have a second component defined in a plane parallel to the first tissue contacting surface 43 in a range of 0 degrees to about ±10 degrees. The transmission axis T-T may be offset from the longitudinal axis A-A at the distal end 55 of the transmissive element 54. As shown, both components of the transmission angle α are zero.

The distal portion of the transmissive element 54 may be secured within the first jaw member 42 such that the distal end 55 of the transmissive element 54 is fixed relative to the optical elements 62. However, in some embodiments the distal end 55 of the transmissive element 54 may be movable during a surgical procedure to change the distribution of energy during the surgical procedure. For example, first or second components of the transmission angle α, the distance $D_1$, and/or the distance $D_2$ may be altered during a surgical procedure such that the distribution of energy may have a first configuration and a second configuration during the same surgical procedure. The first configuration may be configured to seal tissue and the second configuration may be configured to cut tissue.

As best shown in FIG. 4, the optical elements 62 are cylindrical elements arranged substantially transverse to the longitudinal axis A-A of the first jaw member 42. The optical elements 62 may be cylindrical reflectors, deflectors, or mirrors, e.g., Fresnel reflectors, embedded within the cavity 41 of the first jaw member 42. As shown, the optical elements 62 are cylindrical in shape and each have approximately the same diameter as one another. The diameters of the cylindrical reflectors may vary along the length of the first jaw member 42 to facilitate beam shaping or a distribution of energy. In embodiments using cylindrically shaped optical elements 62, the cylindrical reflectors may have a diameter in a range of about 0.25 mm to about 2 mm. In some embodiments, the optical elements 62 have other shapes including, but not limited to, spheres, half-spheres, prismatic, and/or crystalline. The optical elements 62 may have a uniform shape along the optical array 60 or may vary in shape along the optical array 60.

The optical elements 62 are configured to reflect the beam of light L transmitted from the transmissive element 54 to seal, coagulate, and/or cut tissue captured between the first and second jaw members 42, 44. As shown in FIG. 4, the optical elements 62 form a staircase that rises towards the first tissue contacting surface 43 as the optical elements 62 approach a distal end of the first jaw member 42. As the beam of light L is transmitted from the distal end 55 of the transmissive element 54, the beam of light L is reflected by the optical elements 62 towards the first tissue contacting surface 43. The optical elements 62 reflect the beam of light L to form a predetermined distribution of energy across (i.e., in a direction transverse to the centerline of the first jaw member 42) and along (i.e., in a direction parallel with the centerline of the first jaw member 42) to seal, coagulate, and/or cut tissue between the first and second jaw members 42, 44.

Different distributions of energy may be desirable across and along the first jaw member 42. For example, for sealing tissue, it may be desirable to have a "top hat" distribution across and along the first jaw member 42 such that energy across and along the first jaw member 42 is widely distributed to be substantially the same at all points across and along the first jaw member 42 where energy is desired with no energy being delivered where it is not desired. Alternatively, for cutting tissue, it may be desirable to have a single thin line across the first jaw member 42 where the tissue is to be cut and a substantially even distribution along the first jaw member 42.

The optical elements 62 may be assembled in a cartridge 61 that is insertable into the cavity 41 of first jaw member 42. The optical system 50 may include a cover 51 that is secured over the cavity 41 to seal the cavity 41. The cover 51 forms a portion of the tissue contacting surface 43. In some embodiments, the cartridge 61 may be removable from the cavity 41 and the cover 51 may retain the cartridge 61 within the cavity 41. The cover 51 may be optically transparent. For example, the cover 51 may be formed of sapphire glass. In some embodiments, the cover 51 may act as a filter to limit wavelengths of light passing through the cover 51 and/or to modify the distribution of energy across and/or along the first jaw member 42. However, it will be appreciated that by filtering the light passing through the cover 51, the cover 51 may be heated. For this reason, it may be beneficial to minimize the light that is filtered by the cover 51. The cover 51 may be configured to withstand a pressure of at least 120 psi. In some embodiments, the cover 51 may be configured to diffuse or refract the light passing through the cover 51.

Figure 5A:
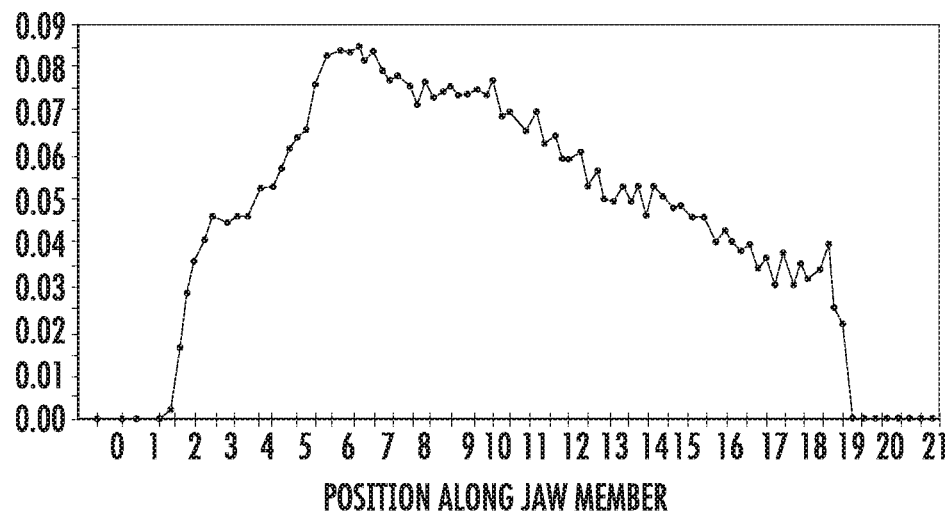
FIGS. 5A and 5B are graphs showing a distribution of energy along and across a jaw member for an exemplary optical array.
Figure 5B:
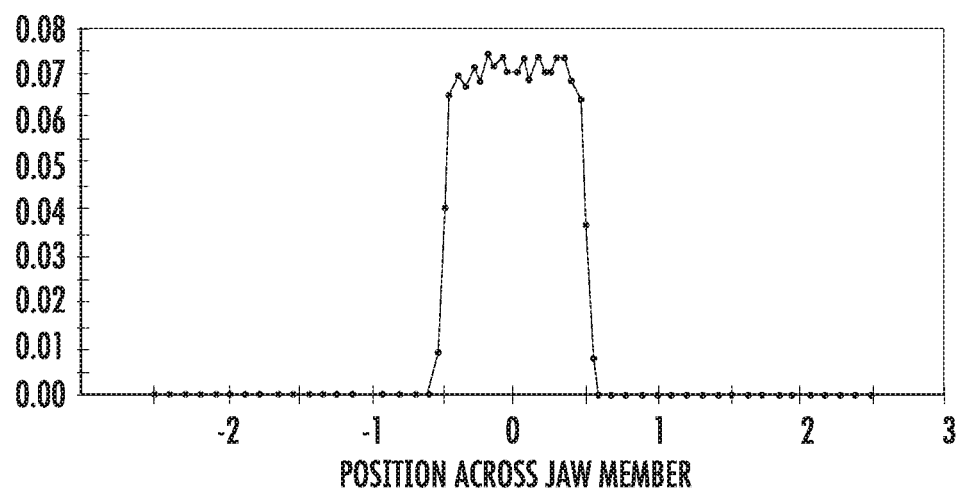

With reference to FIGS. 5A and 5B, the distribution of energy across and along the first jaw member 42 is shown when the optical elements 62 are cylinders having a diameter of about 0.5 mm with the distal end 55 of the transmissive element 54 being positioned about 1.5 mm above a first or bottom cylinder of the optical elements 62 such that the distance $D_2$ is about 1.5 mm. The transmissive element 54 is parallel to the longitudinal axis A-A with the distal end 55 on the longitudinal axis A-A of the first jaw member 42. As best shown in FIG. 5A, the distribution of energy along the first jaw member 42 rises rapidly, briefly plateaus before continuing to rise, and then slowly declines. As best shown in FIG. 5B, the distribution of energy across the first jaw member 42 rises steeply to a substantially flat top and then declines steeply.

Figure 6A:
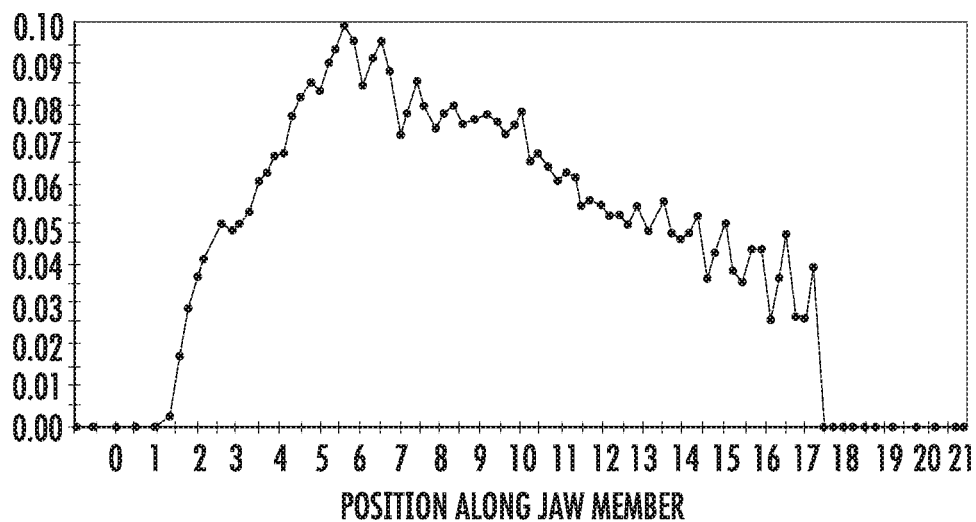
FIGS. 6A and 6B are graphs showing a distribution of energy along and across a jaw member for another exemplary optical array.
Figure 6B:
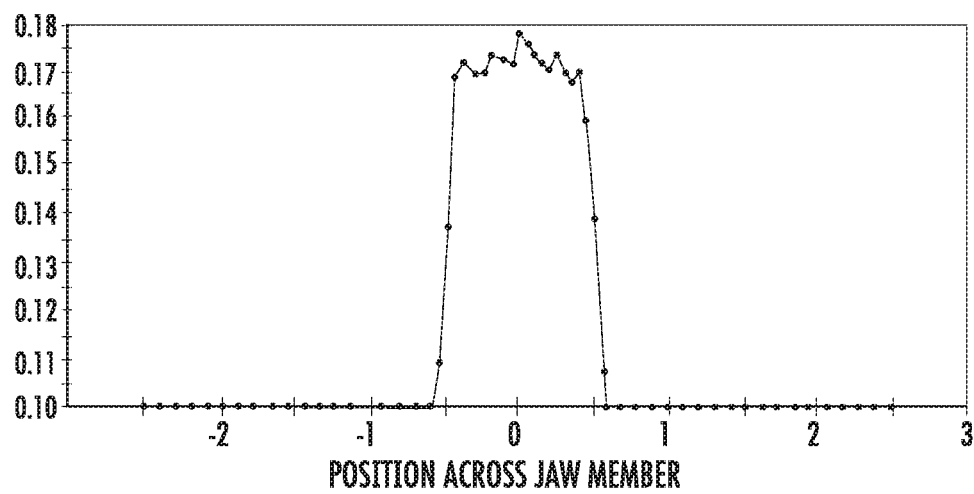

Referring now to FIGS. 6A and 6B, the distribution of energy across and along the first jaw member 42 is shown when the optical elements 62 are cylinders having a diameter of about 0.75 mm with the distal end 55 of the transmissive element 54 being positioned about 1.5 mm above a first or bottom cylinder of the optical elements 62 such that the distance $D_2$ is about 1.5 mm. The transmissive element 54 is parallel to the longitudinal axis A-A with the distal end 55 on the longitudinal axis A-A of the first jaw member 42. As best shown in FIG. 6A, the distribution of energy along the first jaw member 42 rises rapidly, briefly plateaus before continuing to rise, and then slowly declines. When compared to the distribution of energy shown in FIG. 5A, the peak of energy is higher and is more pronounced. As best shown in FIG. 6B, the distribution of energy across the first jaw member 42 rises steeply to a substantially flat top and then declines steeply.

Figure 7A:
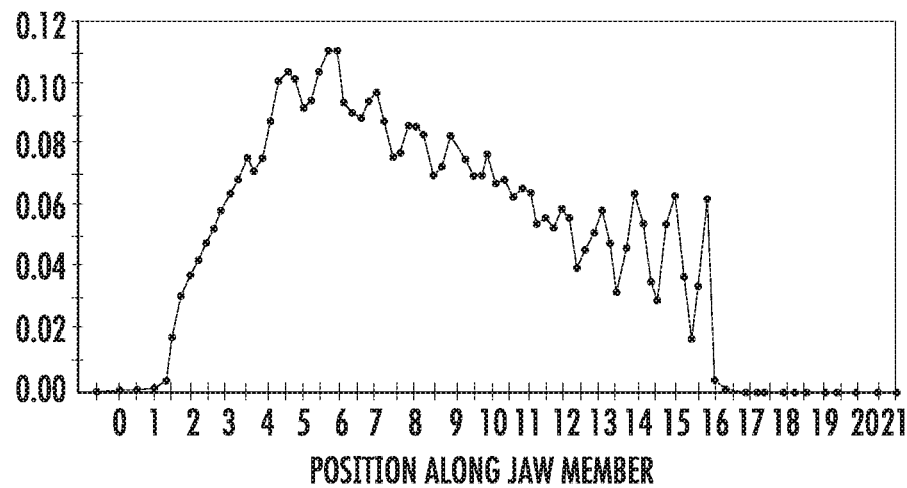
FIGS. 7A and 7B are graphs showing a distribution of energy along and across a jaw member for another exemplary optical array.
Figure 7B:
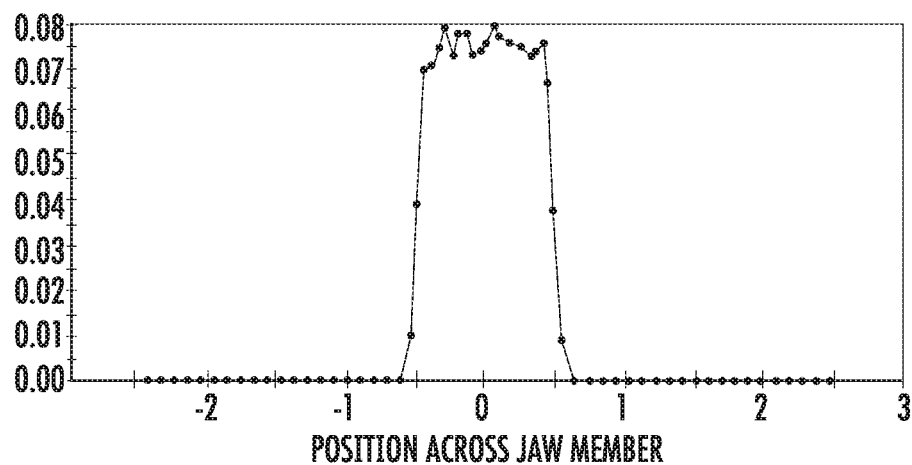

Referring now to FIGS. 7A and 7B, the distribution of energy across and along the first jaw member 42 is shown when the optical elements 62 are cylinders having a diameter of about 1 mm with the distal end 55 of the transmissive element 54 being positioned about 1.5 mm above a first or bottom cylinder of the optical elements 62 such that the distance $D_2$ is about 1.5 mm. The transmissive element 54 is parallel to the longitudinal axis A-A with the distal end 55 on the longitudinal axis A-A of the first jaw member 42. As best shown in FIG. 7A, the distribution of energy along the first jaw member 42 rises rapidly to a peak, slowly declines, and then appears to become less predictable (i.e., has a higher standard deviation) in a distal portion of the first jaw member 42. When compared to the distributions of energy shown in FIGS. 5A and 6A, the initial low peak is removed. As best shown in FIG. 7B, the distribution of energy across the first jaw member 42 rises steeply to a substantially flat top and then declines steeply.

Figure 8A:
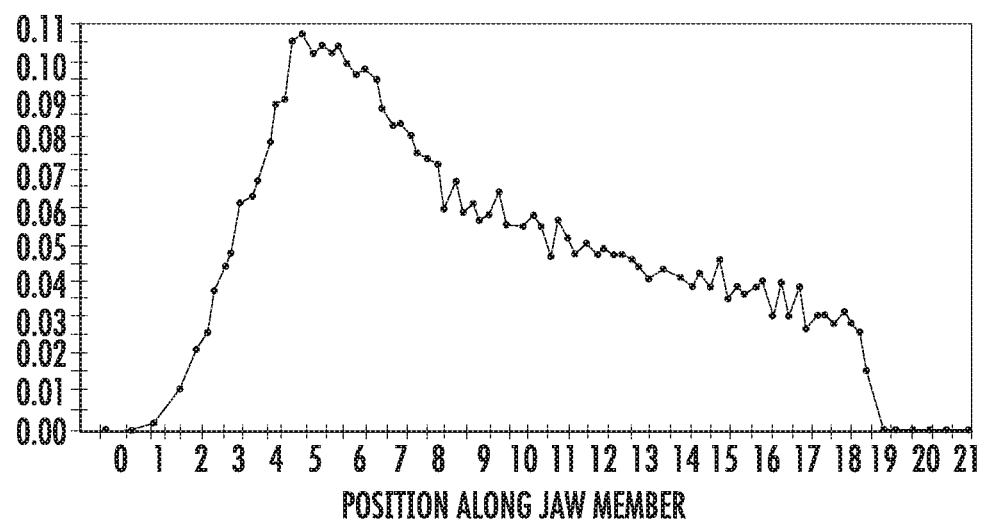
FIGS. 8A and 8B are graphs showing a distribution of energy along and across a jaw member for another exemplary optical array.
Figure 8B:
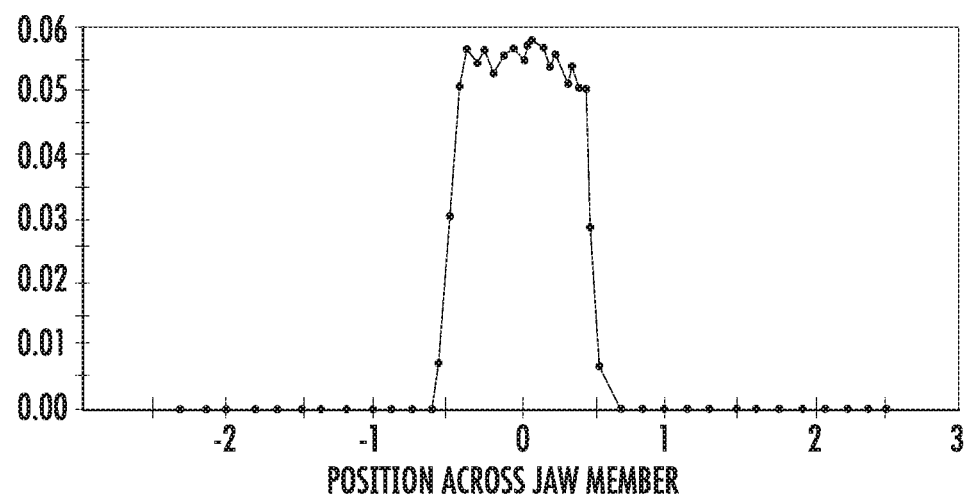

Referring now to FIGS. 8A and 8B, the distribution of energy across and along the first jaw member 42 is shown when the optical elements 62 are cylinders having a diameter of about 0.5 mm with the distal end 55 of the transmissive element 54 being positioned about 1 mm above a first or bottom cylinder of the optical elements 62 such that the distance $D_2$ is about 1 mm. The transmissive element 54 is parallel to the longitudinal axis A-A with the distal end 55 on the longitudinal axis A-A of the first jaw member 42. As best shown in FIG. 8A, the distribution of energy along the first jaw member 42 rises rapidly to a peak, declines quickly, and then gradually declines at a slower rate. When compared to the distributions of energy shown in FIGS. 5A and 6A, the initial low peak is removed. As best shown in FIG. 8B, the distribution of energy across the first jaw member 42 rises steeply to a substantially rounded top and then declines steeply. When compared to the distributions of energy shown in FIGS. 5B, 6B, and 7B, the top of the distribution of energy across the first jaw member 42 is more rounded or less flat.

Figure 9A:
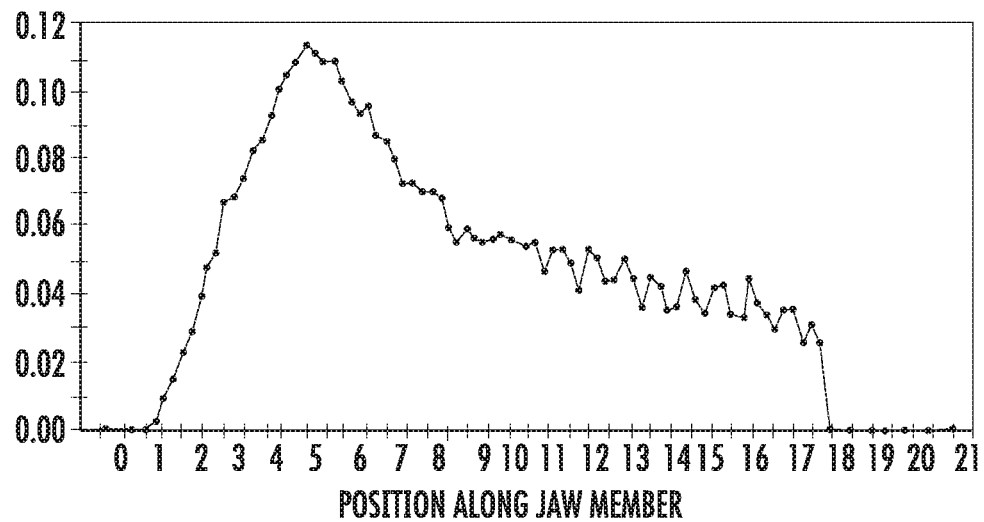
FIGS. 9A and 9B are graphs showing a distribution of energy along and across a jaw member for another exemplary optical array.
Figure 9B:
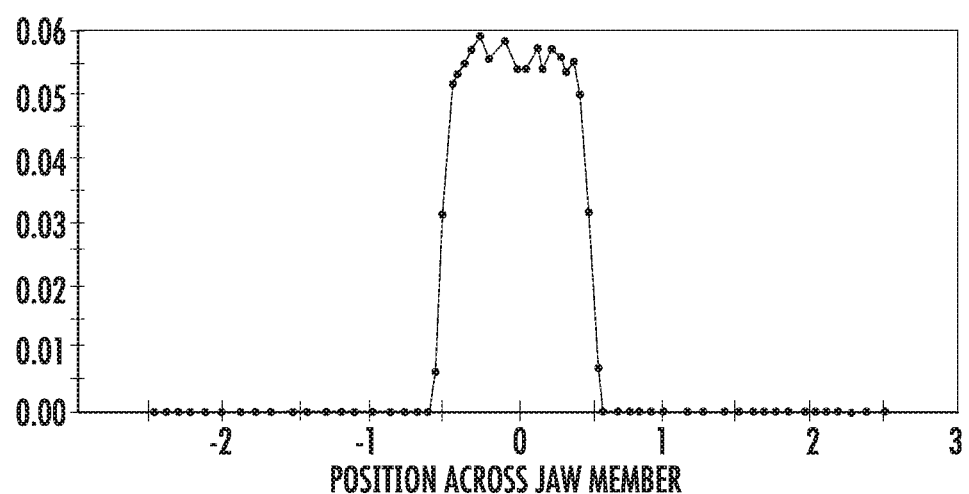

Referring now to FIGS. 9A and 9B, the distribution of energy across and along the first jaw member 42 is shown when the optical elements 62 are cylinders having a diameter of about 0.75 mm with the distal end 55 of the transmissive element 54 being positioned about 1 mm above a first or bottom cylinder of the optical elements 62 such that the distance $D_2$ is about 1 mm. The transmissive element 54 is parallel to the longitudinal axis A-A with the distal end 55 on the longitudinal axis A-A of the first jaw member 42. As best shown in FIG. 9A, the distribution of energy along the first jaw member 42 rises rapidly to a peak, declines quickly, and then gradually declines at a slower rate. When compared to the distribution of energy shown in FIG. 8A, the first decline is quicker and during the gradual decline the distribution is less predictable. As best shown in FIG. 9B, the distribution of energy across the first jaw member 42 rises steeply to a substantially rounded top to a first peak, declines to a short plateau just below the first peak, then rises to a second rounded peak before declining steeply.

Figure 10A:
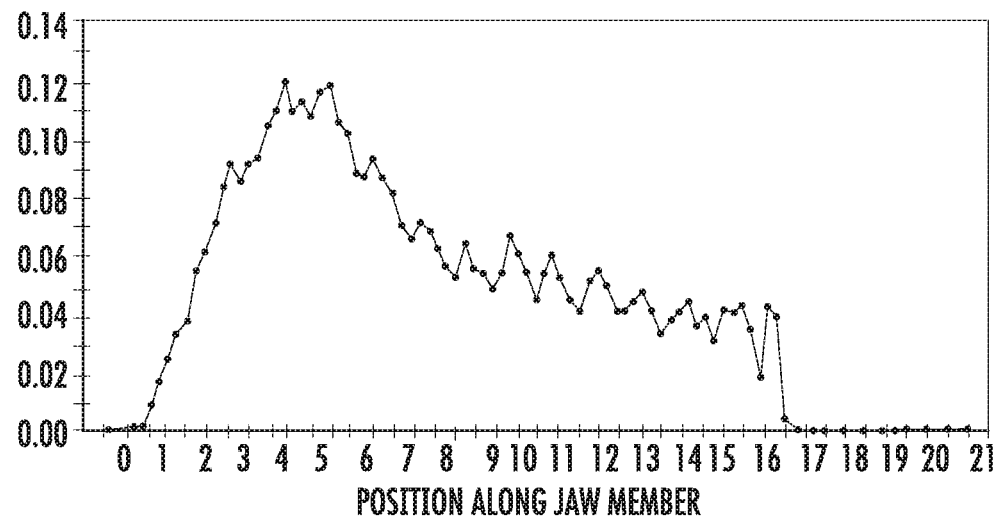
FIGS. 10A and 10B are graphs showing a distribution of energy along and across a jaw member for another exemplary optical array.
Figure 10B:
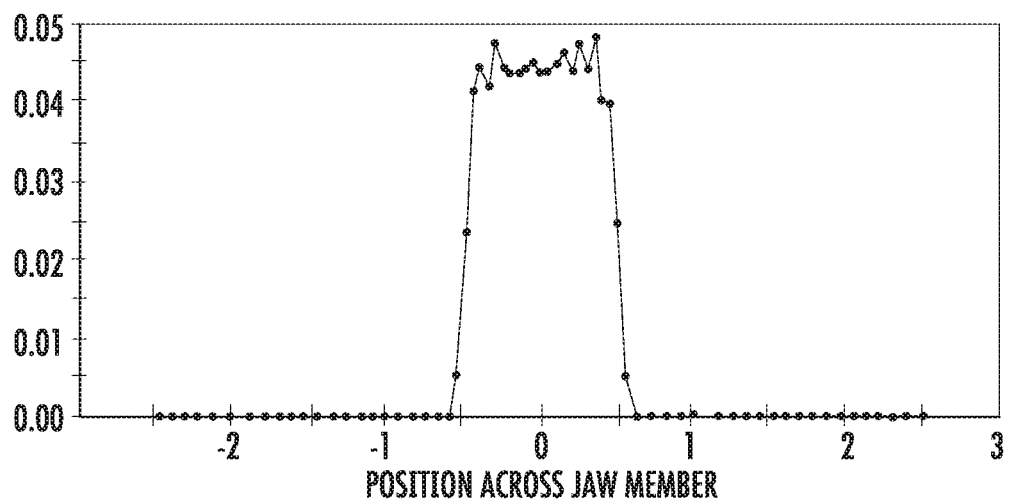

Referring now to FIGS. 10A and 10B, the distribution of energy across and along the first jaw member 42 is shown when the optical elements 62 are cylinders having a diameter of about 1 mm with the distal end 55 of the transmissive element 54 being positioned about 1 mm above a first or bottom cylinder of the optical elements 62 such that the distance $D_2$ is about 1 mm. The transmissive element 54 is parallel to the longitudinal axis A-A with the distal end 55 on the longitudinal axis A-A of the first jaw member 42. As best shown in FIG. 10A, the distribution of energy along the first jaw member 42 rises rapidly to a peak, quickly declines, and then gradually declines. It will be noted that during the entire decline of the energy that the distribution of energy along the first jaw member 42 is less predictable than the previous distributions of energy. As best shown in FIG. 10B, the distribution of energy across the first jaw member 42 rises steeply to a first peak, declines to a plateau, and then rises to a second peak before declining steeply. When compared to the distribution of energy shown in 9B, the first and second peaks are sharper and the plateau is longer.

It will be appreciated that the above diameters of cylindrical optical elements 62 and distances $D_2$ are non-limiting examples of contemplated configurations of the optical array 60.

Figure 11:
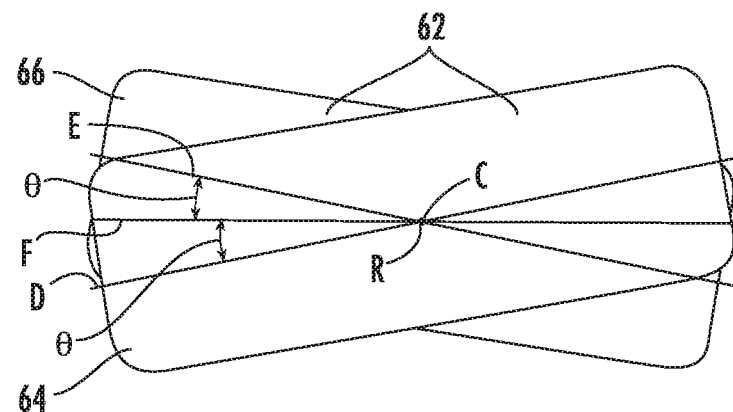
FIG. 11 is a schematic view of a first and second series of optical elements of an optical array provided in accordance with the present disclosure.
Figure 12:
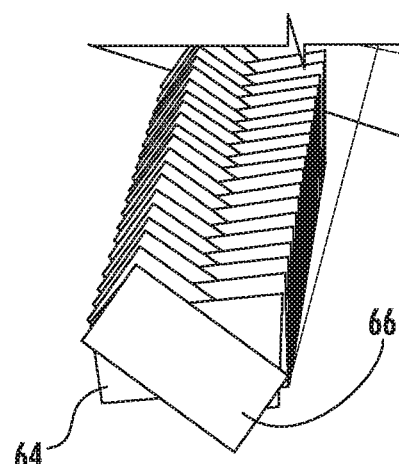
FIG. 12 is a perspective view of the optical array of FIG. 11.

With reference to FIGS. 11 and 12, in embodiments of the present disclosure the optical elements 62 are cylinders arranged substantially transverse to the longitudinal axis A-A and in a first series 64 and a second series 66 that are each rotated about an axis of rotation R of the respective optical element 62 at an angle θ from a base plane F. The axis of rotation R passes through a center C of the respective optical element 62 and is parallel to the longitudinal axis A-A of the first jaw member 42 (FIG. 3). The base plane F is a plane parallel to the tissue contacting surface 43 (FIG. 4) and the angle θ is defined between the base plane F and a longitudinal axis D of cylinders of the first series 64 and a longitudinal axis E of cylinders of the second series 66. The first series 64 is rotated in a first direction from the base plane F and the second series 66 is rotated in a second direction from the base plane F that is opposite to the rotation of the first series 64. As shown, the longitudinal axes D and E intersect substantially at center C of each of the optical elements 62 and along the centerline of the first jaw member 42. As detailed below, the rotation of the first and second series 64, 66 concentrate the distribution of energy across the first jaw member 42 at the centerline thereof. The angle θ may be in a range of about 0 degrees to about 45 degrees. In embodiments, the first series 64 may be rotated at a first angle $\theta_1$ and the second series 66 may be rotated at a second angle $\theta_2$. In some embodiments, the angle θ or angles $\theta_1$, $\theta_2$ may vary along the optical array 60.

Figure 13A:
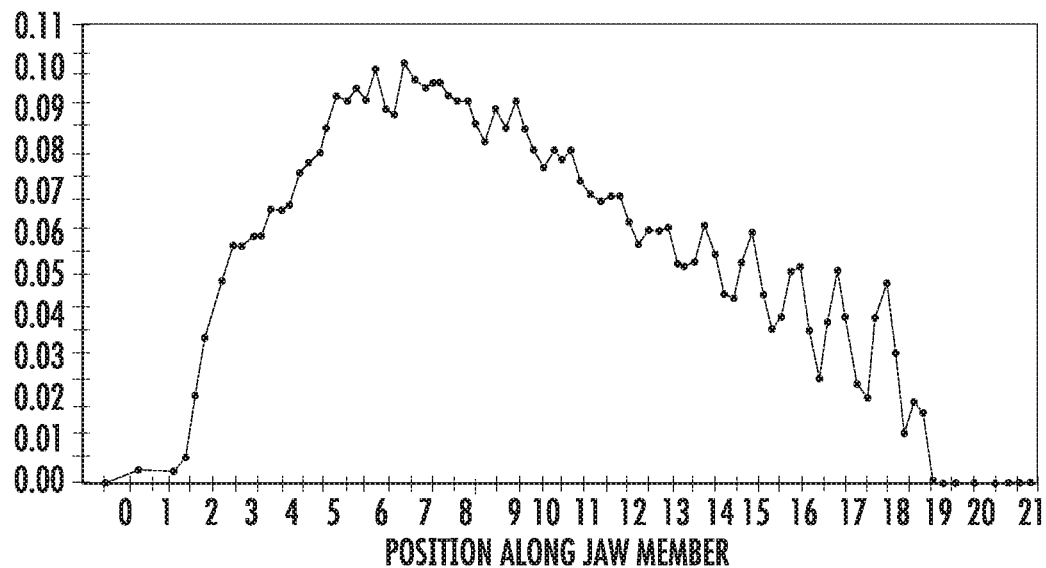
FIGS. 13A and 13B are graphs showing a distribution of energy along and across a jaw member for an exemplary optical array having first and second series of optical elements.
Figure 13B:
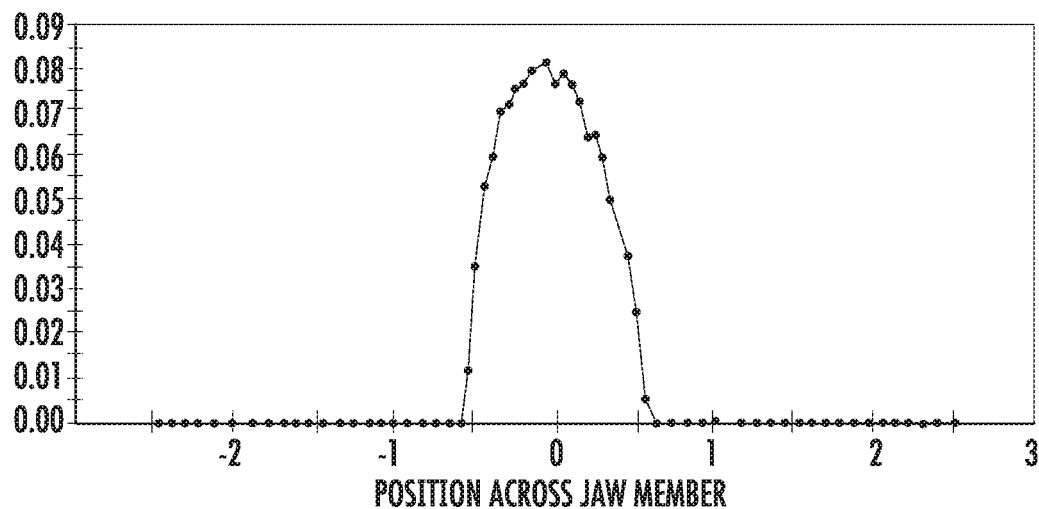

Referring to FIGS. 13A and 13B, the distribution of energy across and along the first jaw member 42 is shown with the optical elements 62 being cylinders having a diameter of about 0.5 mm, with the first and second series 64, 66 rotated at an angle θ of about 5 degrees, and the transmissive element 54 being positioned about 1.5 mm above a first or bottom cylinder of the optical elements 62 such that the distance $D_2$ is about 1.5 mm. With particular reference to FIG. 13A, the distribution of energy along the first jaw member 42 rises rapidly to a peak before declining gradually. As best shown in FIG. 13B, the distribution of energy across the first jaw member 42 rises swiftly to a rounded peak and declines swiftly such that the distribution of energy is concentrated along the centerline of the first jaw member 42. An energy distribution of this nature may be beneficial for cutting tissue disposed between the first and second jaw members 42, 44.

Figure 14A:
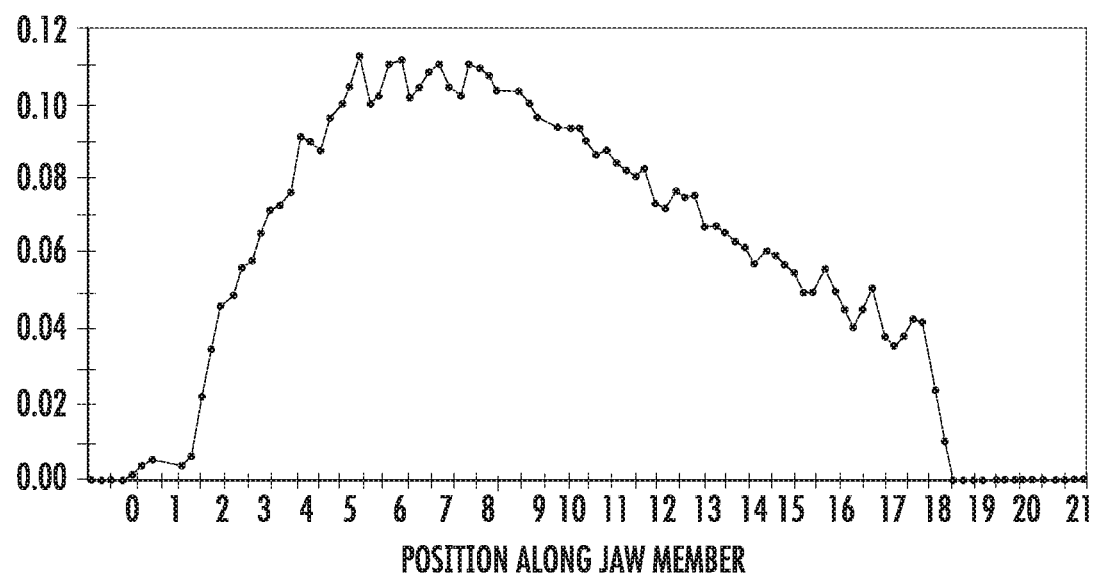
FIGS. 14A and 14B are graphs showing a distribution of energy along and across a jaw member for another exemplary optical array.
Figure 14B:
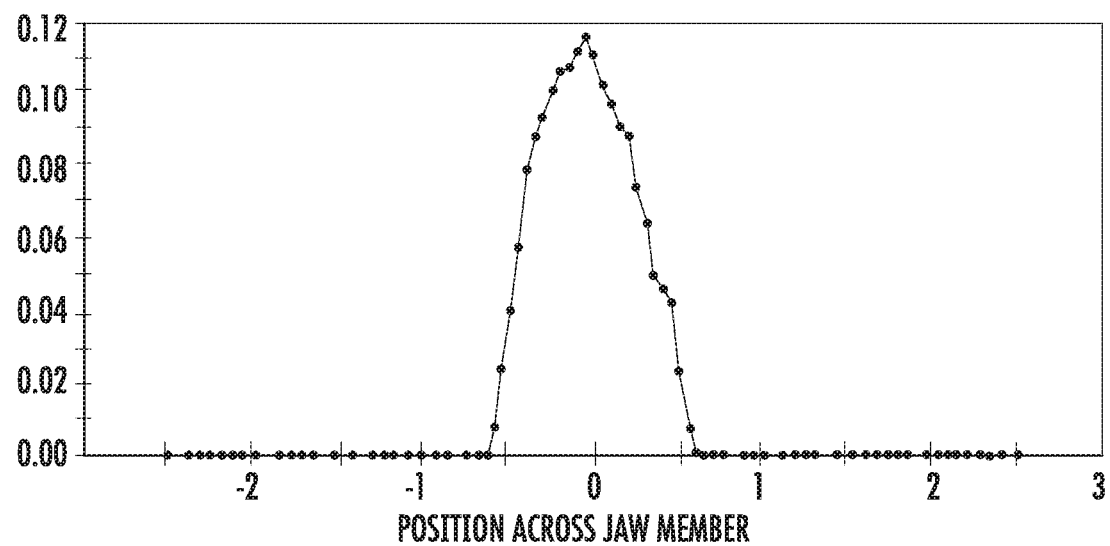

Referring to FIGS. 14A and 14B, the distribution of energy across and along the first jaw member 42 is shown with the optical elements 62 being cylinders having a diameter of about 0.5 mm, with the first and second series 64, 66 are rotated at an angle θ of about 10 degrees, and the transmissive element 54 being positioned about 1.5 mm above a first or bottom cylinder of the optical elements 62 such that the distance $D_2$ is about 1.5 mm. With particular reference to FIG. 13A, the distribution of energy along the first jaw member 42 rises rapidly to a peak before declining gradually. When compared to the distribution of energy of FIG. 13A, the peak is less pronounced and the decline is more predictable. As best shown in FIG. 13B, the distribution of energy across the first jaw member 42 rises swiftly to a rounded peak and declines swiftly such that the distribution of energy is concentrated along the centerline of the first jaw member 42. When compared to the distribution of energy of FIG. 13B, the peak is more pronounced such that more energy is concentrated along the centerline of the first jaw member 42. Energy distribution of this nature may be beneficial for cutting tissue disposed between the first and second jaw members 42, 44.

Figure 15:
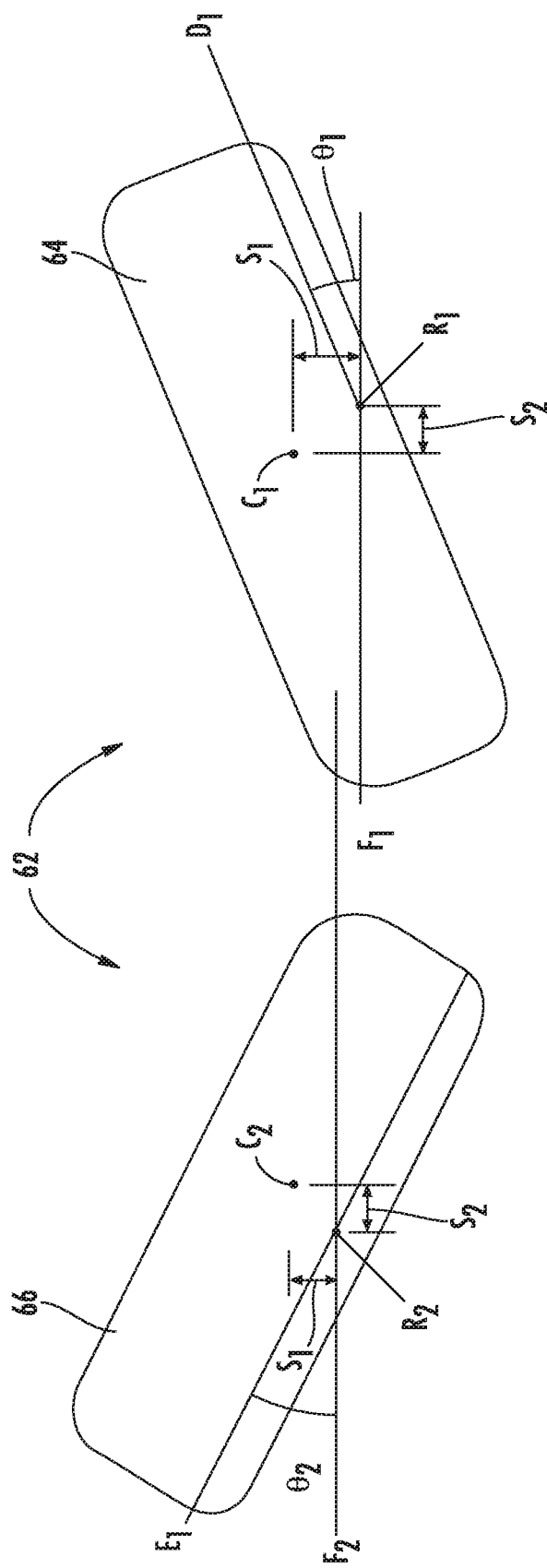
FIG. 15 is a schematic view of a first and second series of optical elements of an optical array provided in accordance with the present disclosure.

With reference to FIG. 15, in embodiments of the present disclosure the optical elements 62 are cylinders arranged substantially transverse to the longitudinal axis A-A and in a first series 64 and a second series 66 that are each rotated about a respective axis of rotation $R_1$, $R_2$ of the respective optical element 62 at an angle θ from a respective base plane $F_1$, $F_2$. As shown, the first and second series 64, 66 of optical elements 62 are spaced apart from one another; however, the first and second series 64, 66 of optical elements 62 may at least partially overlap with one another. The axes of rotation $R_1$, $R_2$ are offset from a center $C_1$, $C_2$ of the respective optical element 62, 64 and is parallel to the longitudinal axis A-A of the first jaw member 42 (FIG. 3). Each of the axes of rotation $R_1$, $R_2$ is offset by a first shift $S_1$ and a second shift $S_2$. The first and second shifts $S_1$, $S_2$ may be the same or different from one another. In addition, the axes of rotation $R_1$ of the first series 64 may have first and second shifts $S_1$, $S_2$ that are the same or different from the first and second shifts $S_1$, $S_2$ of the axes of rotation $R_2$ of the second series 66. The first shift $S_1$ has a positive direction away from the tissue contacting surface 43 (FIG. 4) and the second shift $S_2$ has a positive direction away from the centerline of the first jaw member 42 (FIG. 3). In addition, the first and second shifts $S_1$, $S_2$ may vary along the length of the first jaw member 42. The base planes $F_1$, $F_2$ are planes parallel to the tissue contacting surface 43 (FIG. 4) and the angles $\theta_1$, $\theta_2$ are defined about the respective axis of rotation $R_1$, $R_2$ and can be visualized between the respective base plane $F_1$, $F_2$ and an axis $D_1$, $E_1$ that is parallel to a longitudinal axis of the respective optical element 62 intersecting the respective axis of rotation $R_1$, $R_2$. The first series 64 is rotated in a first direction about the axis for rotation $R_1$ from the base plane F and the second series 66 is rotated about the axis of rotation $R_2$ in a second direction from the base plane F that is opposite to the rotation of the first series 64. As detailed below, the rotation of the first and second series 64, 66 concentrate the distribution of energy across the first jaw member 42 at the centerline thereof. The angle $\theta$ may be in a range of about 0 degrees to about 45 degrees. In embodiments, the first series 64 may be rotated at a first angle $\theta_1$ and the second series 66 may be rotated at a second angle $\theta_2$. In some embodiments, the angle $\theta$ or angles $\theta_1$, $\theta_2$ may vary along the optical array 60.

Figure 16A:
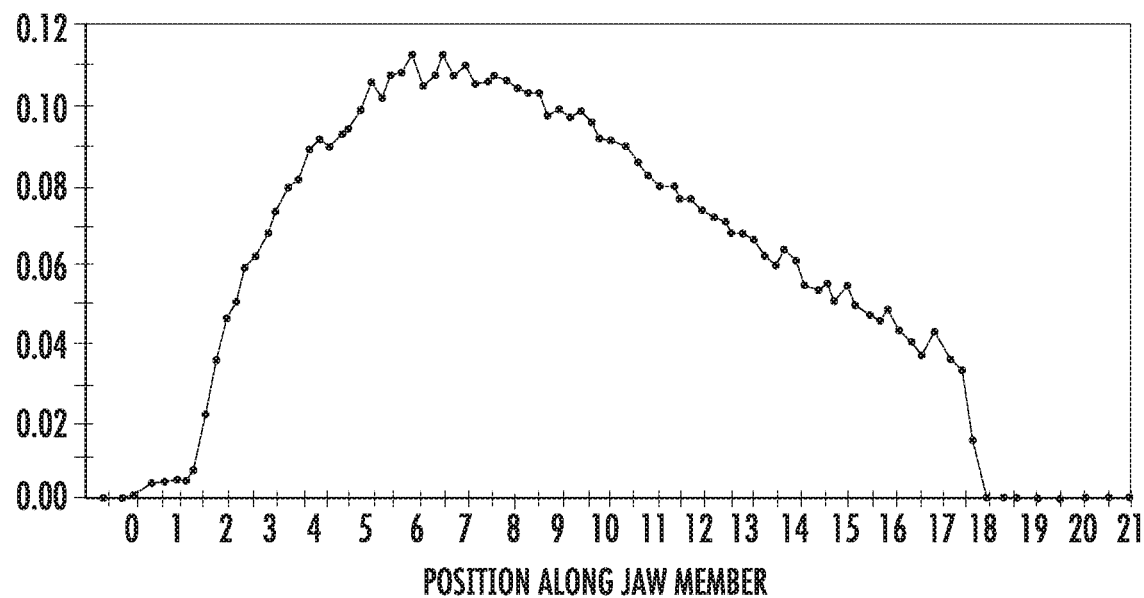
FIGS. 16A and 16B are graphs showing a distribution of energy along and across a jaw member for an exemplary optical array having a shift.
Figure 16B:
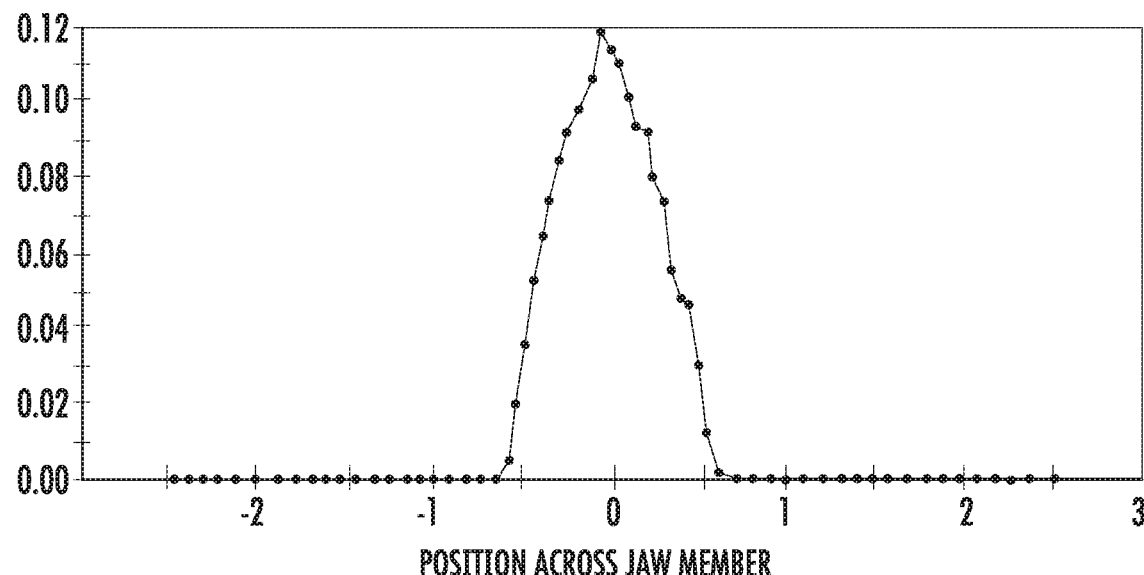

Referring to FIGS. 16A and 16B, the distribution of energy across and along the first jaw member 42 is shown with the optical elements 62 being cylinders having a diameter of about 0.5 mm, with the first and second series 64, 66 are each rotated at an angle $\theta$ of about 10 degrees, with a shift of about 0.1 mm ($S_1$) and about 0.07 mm ($S_2$), and the transmissive element 54 being positioned about 1.5 mm above a first or bottom cylinder of the optical elements 62 such that the distance $D_2$ is about 1.5 mm. With particular reference to FIG. 16A, the distribution of energy along the first jaw member 42 rises rapidly to a rounded peak before declining gradually. When compared to the energy distribution of FIG. 14A, the peak is more rounded such that the energy is more evenly distributed along the first jaw member 42. As best shown in FIG. 16B, the distribution of energy across the first jaw member 42 rises swiftly to a pronounced peak and declines swiftly such that the distribution of energy is concentrated along the centerline of the first jaw member 42. When compared to the energy distribution of FIG. 14B, the peak is significantly more pronounced. An energy distribution of this nature may be beneficial for cutting tissue disposed between the first and second jaw members 42, 44.

Figure 17A:
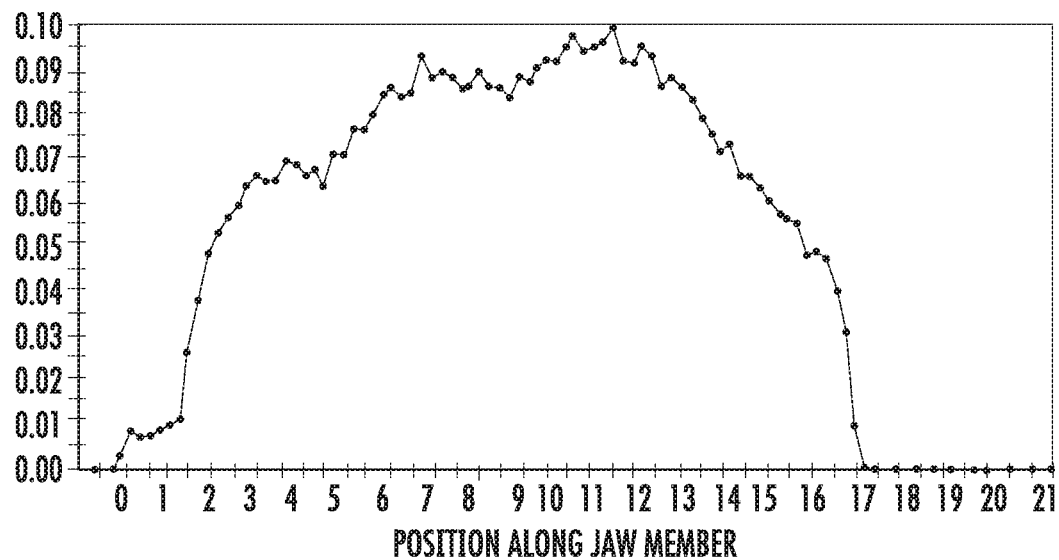
FIGS. 17A and 17B are graphs showing a distribution of energy along and across a jaw member for another exemplary optical array.
Figure 17B:
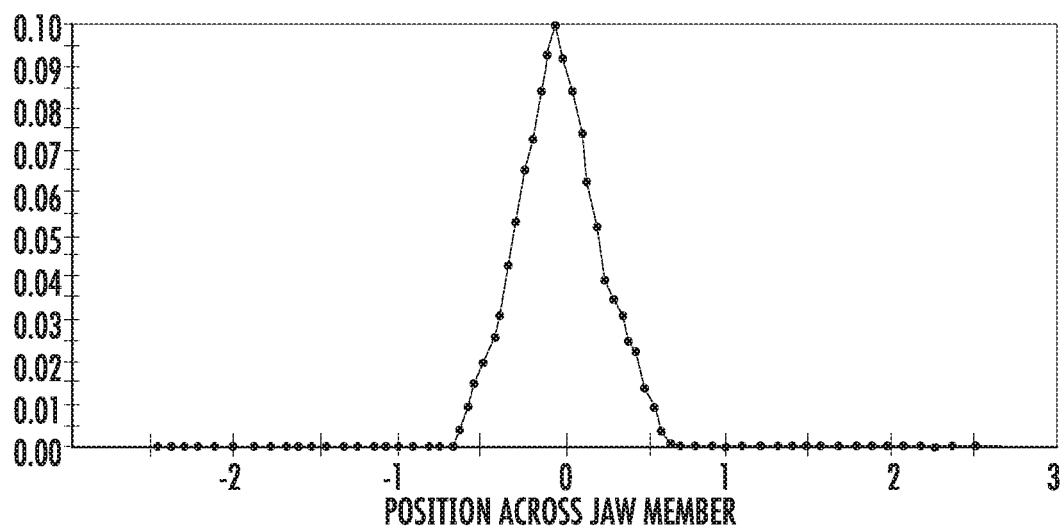

Referring to FIGS. 17A and 17B, the distribution of energy across and along the first jaw member 42 is shown with the optical elements 62 being cylinders having a diameter of about 0.5 mm, with the first and second series 64, 66 are each rotated at an angle $\theta$ of about 20 degrees, with a shift of about 0.25 mm ($S_1$) and about 0.15 mm ($S_2$), and the transmissive element 54 being positioned about 1.5 mm above a first or bottom cylinder of the optical elements 62 such that the distance $D_2$ is about 1.5 mm. With particular reference to FIG. 16A, the distribution of energy along the first jaw member 42 rises rapidly to a first peak, plateaus, rises to a second larger plateau, rises slowly to a final peak before declining quickly. When compared to the energy distribution of FIG. 16A, the distribution of energy along first jaw member 42 is maintained at a more consistent level. As best shown in FIG. 17B, the distribution of energy across the first jaw member 42 rises swiftly to a pronounced peak and declines swiftly such that the distribution of energy is concentrated along the centerline of the first jaw member 42. When compared to the energy distribution of FIG. 17B, the peak is even more pronounced. An energy distribution of this nature may be beneficial for cutting tissue disposed between the first and second jaw members 42, 44.

Figure 18:
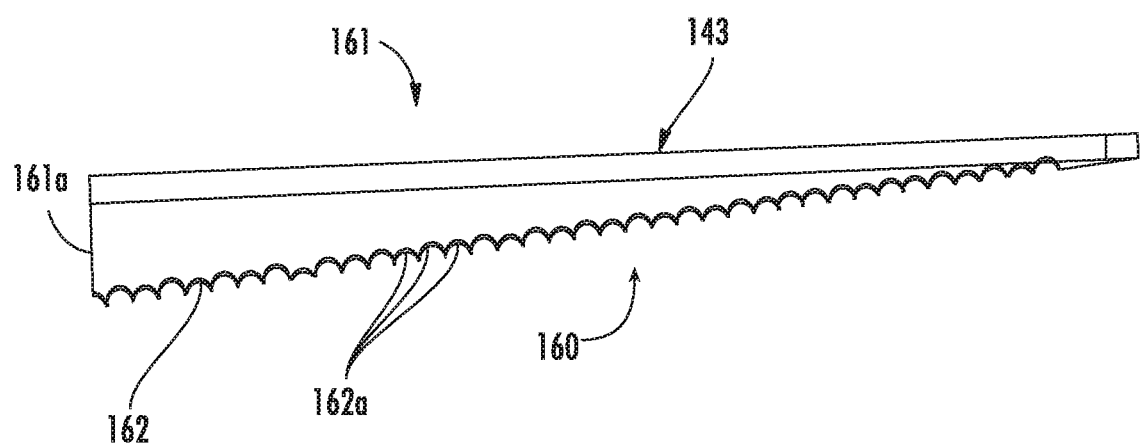
FIG. 18 is a side view of a cartridge provided in accordance with the present disclosure.

With reference to FIG. 18, an optical cartridge 161 having an optical array 160 is provided in accordance with the present disclosure. The optical cartridge 161 is insertable within the cavity 41 (FIG. 3) of the first jaw member 42. The optical cartridge 161 functions in a similar manner to the optical array 60 detailed above. The optical cartridge 161 includes a bottom surface 162 that has a plurality of optical elements 162a defined therein. The plurality of optical elements 162a is semi-cylindrical in shape and is configured to reflect a beam of light that enters a proximal end 161a of the optical cartridge 161 towards a tissue contacting surface 143 of the optical cartridge 161. The optical cartridge 161 is a solid glass reflector and may be formed of sapphire. Side surfaces and the bottom surface 162 of the optical cartridge 161 may include a reflective coating, e.g., a reflective metal coating. A solid cartridge may improve coupling with the transmissive element 54, may reduce losses, and may be easier to clean than the optical array 60 detailed above.

The plurality of optical elements 162a may be arranged in a single series or may be arranged in a first series and a second series. In addition, the plurality optical elements 162a may be spherical, semi-spherical, prismatic, and/or crystalline in shape.

Figure 19:
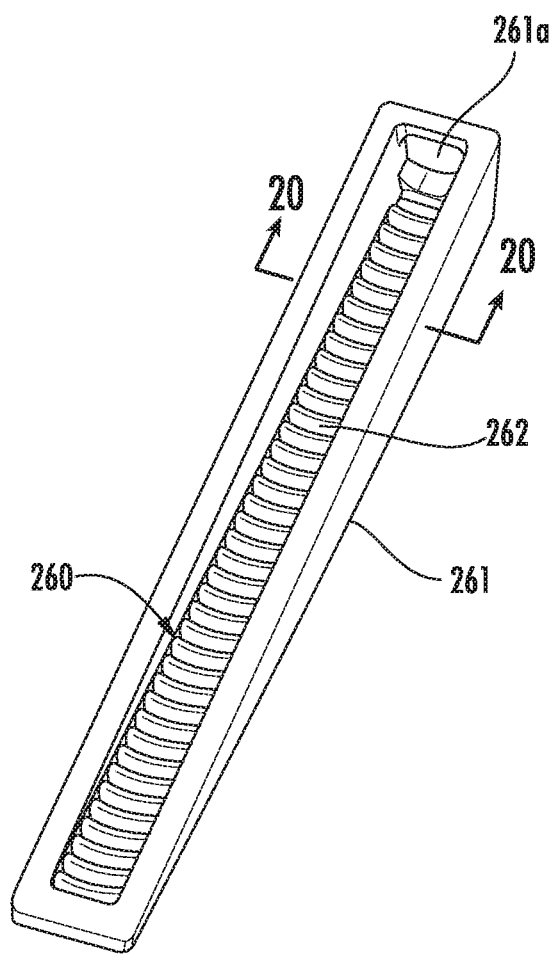
FIG. 19 is a front perspective view of another cartridge provided in accordance with the present disclosure.
Figure 20:
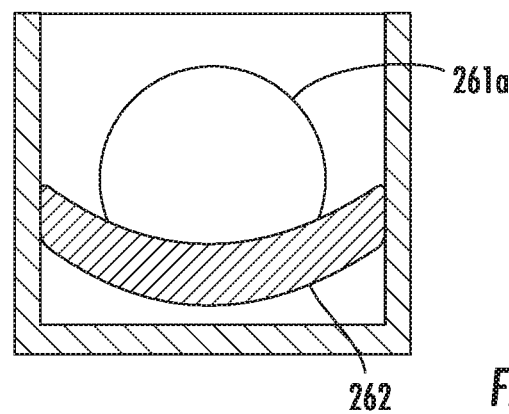
FIG. 20 is a cross-sectional view taken along the section line 20-20 of FIG. 19.

With reference to FIGS. 19 and 20, a cartridge 261 having an optical array 260 is provided in accordance with the present disclosure. The optical array 260 includes optical elements 262 that are substantially cylindrical in shape with a curved longitudinal axis such that optical elements 262 have a substantially U-shaped cross-section in a plane transverse to the longitudinal axis of the first jaw member 42 as shown in FIG. 20. The optical elements 262 may be rotated in first and second series, e.g., first and second series 64, 66, which concentrate the distribution of energy across the first jaw member 42 at the centerline thereof. The optical elements 262 may have a parabolic cross-section which is configured to focus energy at the centerline of the first jaw member 42 along the tissue contacting surface 43.

Figure 21:
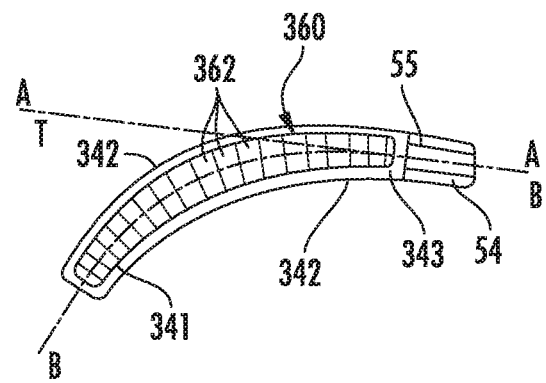
FIG. 21 is a top view of a curved jaw member having an optical array provided in accordance with the present disclosure.

Referring now to FIG. 21, a curved jaw member 342 is disclosed in accordance with the present disclosure. The curved jaw member 342 is similar to the first jaw member 42 detailed above, as such only the differences will be detailed herein for reasons of brevity. The curved jaw member 342 may be used with another curved jaw member that opposes the curved jaw member 342 to selectively grasp tissue therebetween. The curved jaw member 342 defines a cavity 341 that includes a plurality of optical elements 362 disposed therein. The plurality of optical elements 362 is similar to the optical elements 62 detailed above. Alternatively, cavity 341 may receive a curved cartridge similar to the cartridges 61, 161, 262 detailed above. The optical elements 362 may be configured to reflect a beam of light L towards a tissue contacting surface 343 of the curved jaw member 342 and to direct the beam of light L around the curve of the curved jaw member 342 such that a distribution of energy at the tissue contacting surface is evenly distributed along and across the tissue contacting surface 343. The distal end 55 of the transmissive element 54 may be offset from the longitudinal axis A-A of the jaw member and/or the transmissive angle T may be nonzero to improve a distribution of energy around the curved jaw member 342.

As shown above, each of the optical elements has a cylindrical or substantially cylindrical shape; however, each reflector may have a plurality of shapes including, but not limited to, semi-cylindrical, semi-spherical, prismatic, or crystalline. A single optical array may include optical elements having a plurality of shapes.

In particular embodiments, the tissue contacting surface of the first and second jaw members may include features to prevent tissue grasped or clamped between the first and second jaw members from moving relative to the first and second jaw members. For example, one or more of the tissue contacting surfaces may be textured to grasp tissue. Additionally or alternatively, one or more of the tissue contacting surfaces may include ridges, ribs, or other features extending towards the opposite jaw member to secure tissue between the first and second jaw members.

The optical arrays detailed herein may allow light energy to be uniformly distributed and radiated from the tissue contacting surface of a jaw member for an optical-based tissue treatment system. In addition, optical arrays may increase efficiency of energy delivery when compared to the efficiency of radiofrequency-based devices used for similar purposes. Further, the staircase of reflectors may improve seal quality, minimize thermal spread during a seal cycle, improve safety due to lower jaw member temperatures, and facilitate cutting without a mechanical blade.

A surgical kit may be provided with a plurality of optical cartridges. Each of the optical cartridges may be configured to deliver light having a different distribution to tissue positioned between the jaw members. Each of the optical cartridges may be configured for use with a particular type of tissue such that the distribution of energy is optimized to seal and/or cut the particular type of tissue.

The surgical instrument may be configured to detect a type of optical cartridge and/or an optical array received within a jaw member of the end effector and adjust parameters of the light source, e.g., light source 52 (FIG. 1), in response to the detected optical cartridge or optical array. The parameters of light adjusted by the surgical instrument may include, but are not limited to, the power, wavelength, and/or duration of the light emitted from the light source. In addition, the surgical instrument may adjust parameters of the light source in response to a detected or inputted type of tissue.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 22:
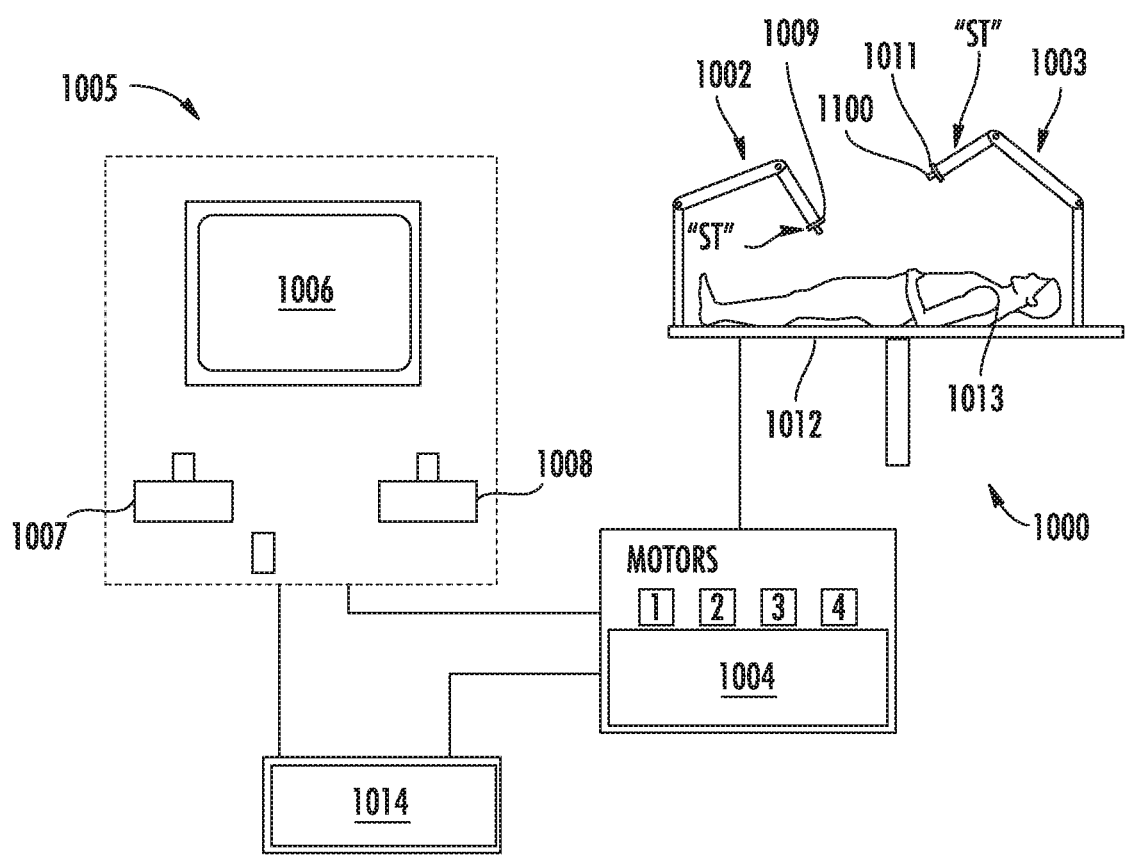
FIG. 22 is a schematic of an exemplary telesurgery system in accordance with the present disclosure.

Turning to FIG. 22, a robotic surgical system configured for use in accordance with the present disclosure is shown generally identified by reference numeral 1000. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST." One or more of the surgical tools "ST" may include a DLU, e.g., DLU 100, similar to those detailed above, thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors. The surgical tools "ST" may include optical-based sealing instruments configured to seal and/or cut tissue without a mechanical blade detailed above.

The various embodiments of surgical instruments and surgical systems disclosed herein may be used to perform surgical procedures to seal and/or cut tissue with optical energy. Initially, an end effector assembly or cartridge may be selected from a plurality of end effector assemblies or cartridges based on the type of tissue to be sealed and/or cut. The end effector assembly or cartridge may also be selected based on the function of the cartridge, e.g., to seal or to cut. In embodiments where the end effector assembly is selected, the end effector assembly is secured to a distal portion of the surgical instrument. The end effector assembly may be provided as a loading unit, e.g., a disposable loading unit. In embodiments where a cartridge is selected, the cartridge is secured within a cavity defined by a jaw member of the end effector assembly.

With the cartridge and/or end effector assembly secured to the surgical instrument, tissue is grasped between opposing jaw members of the end effector assembly. With tissue grasped between the opposing jaw members, a control interface of the surgical instrument, e.g., trigger 26, switch 28, or button 29, is actuated to activate a light source, e.g., light source 52, to deliver a beam of light to the end effector assembly. The beam of light is emitted from the end of a transmissive element, e.g., transmissive element 54, such that optical elements disposed within the first jaw member reflect the beam of light towards a tissue contacting surface of the first jaw member. The optical energy of the reflected beam of light sealing the tissue grasped between the opposing jaw members.

When the tissue is sealed, another one of the control interfaces of the surgical instrument, e.g., switch 28 or button 29, may be actuated to change a mode of the surgical instrument from a first mode of operation, e.g., sealing, to a second mode of operation, e.g., cutting. The light source is then activated such that the surgical instrument cuts tissue with optical energy of the reflected beam of light. To transition the surgical instrument from the first mode of operation to the second mode of operation the user may adjust: a power level of the light source, a wavelength of the light source, a transmission angle of the beam of light within the jaw member, which jaw member receives a beam of light from the light source, and/or a filter of a cover of the first jaw member.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. An end effector assembly for an optical surgical instrument, the end effector assembly comprising:
    a jaw member including:
        a tissue contacting surface;
        a cavity defined in the jaw member, the cavity having a cavity surface sloping inward from a distal end portion of the cavity to a proximal end portion of the cavity;
        a fiber optic cable having a portion extending into the cavity;
        a plurality of optical elements positioned within the cavity, the plurality of optical elements disposed on the cavity surface, the plurality of optical elements configured to direct a beam of light exiting the fiber optic cable towards the tissue contacting surface; and
        a cartridge configured to be secured within the cavity, the cartridge including the plurality of optical elements.

2. The end effector assembly according to claim 1, wherein each optical element of the plurality of optical elements is cylindrical in shape and arranged transverse to a longitudinal axis defined through the jaw member.

3. The end effector assembly according to claim 2, wherein each optical element of the plurality of optical elements has the same diameter.

4. The end effector assembly according to claim 1, wherein the plurality of optical elements includes a first series of optical elements and a second series of optical elements, the first series of optical elements rotated relative to the cavity surface in a first direction and the second series of optical elements rotated relative to the cavity surface in a second direction.

5. The end effector assembly according to claim 4, wherein the first series of optical elements is rotated at a first angle and the second series of optical elements is rotated at a second angle.

6. The end effector assembly according to claim 5, wherein the second angle is different from the first angle.

7. The end effector assembly according to claim 1, wherein at least one optical element of the plurality of optical elements is curved away from the tissue contacting surface such that the at least one optical element is U-shaped in cross-section transverse to a longitudinal axis defined through the jaw member.

8. The end effector assembly according to claim 7, wherein the at least one optical element has a parabolic cross-section transverse to the longitudinal axis.

9. The end effector assembly according to claim 1, further comprising a cover disposed over the cavity.

10. The end effector assembly according to claim 9, wherein the cover is configured to modify light reflected from the plurality of optical elements.

11. The end effector assembly according to claim 10, wherein the cover is configured to at least one of filter, refract, or diffuse light reflected from the plurality of optical elements.

12. The end effector assembly according to claim 9, wherein the cover is configured to seal the cavity.

13. The end effector assembly according to claim 1, wherein the jaw member is curved.

14. The end effector assembly according to claim 1, further comprising an opposing jaw member having an opposing tissue contacting surface in opposition to the tissue contacting surface of the jaw member.

15. The end effector assembly according to claim 14, wherein the opposing tissue contacting surface is configured to absorb light.

* * * * *